(12) United States Patent
Bafico et al.

(10) Patent No.: US 8,809,287 B2
(45) Date of Patent: Aug. 19, 2014

(54) COMPOSITIONS AND METHODS FOR ALTERING WNT AUTOCRINE SIGNALING

(75) Inventors: Anna Bafico, New York, NY (US); Stuart Aaronson, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 1713 days.

(21) Appl. No.: 11/719,327

(22) PCT Filed: Nov. 15, 2005

(86) PCT No.: PCT/US2005/041531
§ 371 (c)(1),
(2), (4) Date: Oct. 1, 2007

(87) PCT Pub. No.: WO2006/055635
PCT Pub. Date: May 26, 2006

(65) Prior Publication Data
US 2009/0163407 A1 Jun. 25, 2009

Related U.S. Application Data

(60) Provisional application No. 60/627,977, filed on Nov. 15, 2004.

(51) Int. Cl.
| | | |
|---|---|---|
| C12N 15/11 | (2006.01) | |
| A61K 48/00 | (2006.01) | |
| A61K 38/17 | (2006.01) | |
| A61K 45/06 | (2006.01) | |

(52) U.S. Cl.
CPC ............. *A61K 38/1703* (2013.01); *A61K 45/06* (2013.01)
USPC ...................................... 514/44 A; 514/44 R

(58) Field of Classification Search
USPC ............................................... 514/44 A, 44 R
See application file for complete search history.

(56) References Cited

U.S. PATENT DOCUMENTS

| | | | |
|---|---|---|---|
| 3,817,837 A | 6/1974 | Rubenstein et al. | |
| 3,859,752 A | 1/1975 | Morrison et al. | |
| 3,939,350 A | 2/1976 | Kronick et al. | |
| 3,996,345 A | 12/1976 | Ullman et al. | |
| 4,274,149 A | 6/1981 | Flanagan | |
| 4,277,437 A | 7/1981 | Maggio | |
| 4,366,241 A | 12/1982 | Tom et al. | |
| 4,980,286 A | 12/1990 | Morgan et al. | |
| 5,093,246 A | 3/1992 | Cech et al. | |
| 5,139,941 A | 8/1992 | Muzyczka et al. | |
| 5,252,479 A | 10/1993 | Srivastava | |
| 5,283,185 A | 2/1994 | Epand et al. | |
| 5,585,277 A | 12/1996 | Bowie et al. | |
| 5,635,493 A | 6/1997 | Vournakis et al. | |
| 5,670,488 A | 9/1997 | Gregory et al. | |
| 5,672,344 A | 9/1997 | Kelley et al. | |
| 5,679,582 A | 10/1997 | Bowie et al. | |
| 5,733,761 A | 3/1998 | Treco et al. | |
| 5,753,500 A | 5/1998 | Shenk et al. | |
| 5,767,099 A | 6/1998 | Harris et al. | |
| 5,939,401 A | 8/1999 | Marshall et al. | |
| 6,020,141 A | 2/2000 | Pantoliano et al. | |
| 6,331,254 B1 | 12/2001 | White et al. | |
| 6,565,844 B1 | 5/2003 | Treco et al. | |
| 2004/0247593 A1* | 12/2004 | He et al. ..................... 424/143.1 |
| 2004/0259247 A1* | 12/2004 | Tuschl et al. .................. 435/375 |

FOREIGN PATENT DOCUMENTS

| | | |
|---|---|---|
| WO | WO-92/06180 | 4/1992 |
| WO | WO-92/20316 | 11/1992 |
| WO | WO-92/22635 | 12/1992 |
| WO | WO-93/14188 | 7/1993 |

OTHER PUBLICATIONS

Schweizer et al. (BMC Cell Biol., 2003; 4:1-11).*
Abbas-Terki, Toufik et al., "Lentiviral-Mediated RNA Interference," Human Gene Therapy, Dec. 2002, 13:2197-2201.
Agami, Reuven, "RNAi and related mechanisms and their potential use for therapy," Current Opinion in Chemical Biology, Oct. 2002, 6:829-834.
Alonso, Laura et al., "Stem cells in the skin: waste not, Wnt not," Genes & Development, 2003, 17:1189-1200.
Ashizawa, Satoshi et al., "Collective Inhibition of pRB Family Proteins by Phosphorylation in Cells with $p16^{INK4a}$ Loss or Cyclin E Overexpression," The Journal of Biological Chemistry, Apr. 2001, 276(14):11362-11370.
Bafico, Anna et al., "An autocrine mechanism for constructive Wnt pathway activation in human cancer cells," Cancer Cell, Nov. 2004, 6:497-506.
Bafico, Anna et al., "Characterization of Wnt-1 and Wnt-2 induced growth alterations and signaling pathways in NIH3T3 fibroblasts," Oncogene, 1998, 16:2819-2825.
Bafico, Anna et al., "Interaction of Frizzled Related Protein (FRP) with Wnt Ligands and the Frizzled Receptor Suggests Alternative Mechanisms for FRP Inhibition of Wnt Signaling," The Journal of Biological Chemistry, Jun. 1999, 274(23):16180-16187.
Bafico, Anna et al., "Novel Mechanism of Wnt Signaling Inhibition Mediated by Dickkopf-1 Interaction with LRP6/Arrow," Jul. 2001, 3:683-686.
Bajetta, Emilio et al., "Metastatic Melanoma: Chemotherapy," Seminars in Oncology, Oct. 2002, 29(5):427-445.

(Continued)

*Primary Examiner* — J E Angell
(74) *Attorney, Agent, or Firm* — Fish & Richardson P.C.

(57) ABSTRACT

The present invention relates to compounds and methods for treating cancers in which the autocrine Wnt canonical signaling pathway is activated. In particular, there is provided a method for inhibiting growth of a tumor cell or sensitizing a cancer cell to treatment by contacting such a tumor cell with a compound that alters Wnt signaling. The compound that alters Wnt signaling can be a Wnt antagonist, a Wnt receptor antagonist, or a combination thereof.

21 Claims, 11 Drawing Sheets

(56) References Cited

OTHER PUBLICATIONS

Bartkova, Jirina et al., "The p16-cyclin D/Cdk4-pRb Pathway as a Functional Unit Frequently Altered in Melanoma Pathogenesis," Cancer Research, Dec. 1996, 56:5475-5483.

Bennett, Dorothy et al., "Molecular Regulation of Melanocyte Senescence," Pigment Cell Res, 2002, 15:242-250.

Bernstein, Emily et al., "The Rest is Silence," RNA, 2001, 7:1509-1521 (downloaded from www.majournal.org on Feb. 14, 2006).

Bhanot, Purnima et al., "A new member of the *frizzled* family from *Drosophila* functions as Wingless receptor," Nature, Jul. 1996, 382:225-230.

Bienz, Mariann et al., "Linking Colorectal Cancer to Wnt Signaling," Cell, Oct. 2000, 103:311-320.

Biroccio, Annamaria et al., "Reconstituion of hTERT restores tumorigenicity in melanoma-derived c-Myc low-expressing clones," Oncogene, 2002, 21:3011-3019.

Blasband, Andrew et al., "The Biochemical properties and transforming potential of human Wnt-2 are similar to Wnt-1," Oncogene, 1992, 7:153-161.

Bosher, Julia, M. et al., "RNA interference: genetic wand and genetic watchdog," Nature Cell Biology, Feb. 2000, 2:E31-E36.

Brigham, Kenneth L. et al., "Rapid Communication: In vivo Transfection of Murine Lungs with a Functioning Prokaryotic Gene Using a Liposome Vehicle," The American Journal of Medical Sciences, Oct. 1989, 298(4):278-281.

Brummelkamp, Thijn R. et al., "A System for Stable Expression of Short Interfering RNAs in Mammalian Cells," Science, Apr. 2002, 296:550-553.

Brummelkamp, Thijn R. et al., "Stable suppression of tumorigenicity by virus-mediated RNA interference," Cancer Cell, Sep. 2002, 2:243-247.

Burdette-Radoux, Susan et al., "Phase II trial of flavopiridol, a cyclin dependent kinase inhibitor, in untreated metastatic malignant melanoma," Investigational New Drugs, 2004, 22:315-322.

Cadigan, Ken M. et al., "Wnt signaling: a common theme in animal development," Genes & Development, 1997, 11:3286-3305.

Caldwell, Germaine M. et al., "The Wnt Antagonist s*FRP1* in Colorectal Tumorigenesis," Cancer Research, Feb. 2004, 64:883-888.

Carr, Kristen M. et al., "Gene-expression profiling in human cutaneous melanoma," Oncogene, 2003, 22:3076-3080.

Castellano, M. et al., "*CDKN2A*/p16 Is Inactivated in Most Melanoma Cell Lines," Cancer Research, 1997, 57(21):4868-4875.

Chan, Timothy A. et al., "Targeted inactivation of *CTNNB1* reveals unexpected effects of β-catenin mutation," Proceedings of the National Academy of Sciences, Jun. 2002, 99:8265-8270.

Chen, Shaoqiong et al., "Wnt-1 Signaling inhibits Apoptosis by Activating β-Catenin/T Cell Factor-mediated Transcription," The Journal of Cell Biology, Jan. 2001, 152:87-96.

Clark, Edwin A. et al., "Genomics analysis of metastasis reveals an essential role for RhoC," Nature, Aug. 2000, 406:532-35.

Collisson, Eric A. et al., "Treatment of Metastatic Melanoma with an Orally Available Inhibitor of the Ras-Raf-MAPK Cascade," Cancer Research, Sep. 2003, 63:5669-5673.

Denli, Ahmet M. et al., "RNAi: an ever-growing puzzle," Trends in Biochemical Sciences, Apr. 2003, 28(4):196-201.

Dong, Jianli et al., "*BRAF* Oncogenic Mutations Correlate with Progression rather than Initiation of Human Melanoma," Cancer Research, Jul. 2003, 63:3883-3885.

Eberle, Jurgen et al., "Incomplete Expression of the Tyrosinase Gene Family (Tyrosinase, TRP-1, and TRP-2) in Human Malignant Melanoma Cells in Vitro," Pigment Cell Res., 1995, 8:307-313.

Elbashir, Sayda M. et al., "Duplexes of 21-nucleotide RNAs mediate RNA interference in cultured mammalian cells," Nature, May 2001, 411:494-498.

Englaro, Walter et al., "Inhibition of the Mitogen-activated Protein Kinase Pathway Triggers B16 Melanoma Cell Differentiation," The Journal of Biological Chemistry, Apr. 1998, 273(16):9966-9970.

Faast, Renate et al., "Cdk6-cyclin D3 activity in murine ES cells is resistant to inhibition by p16$^{INK4a}$," Oncogene, 2004, 23:491-502.

Fargnoli, Maria Concetta et al., "CDKN2a/p16$^{INK4a}$ Mutations and Lack of p19$^{ARF}$ Involvement in Familial Melanoma Kindreds," The Journal of Investigative Dermatology, Dec. 1998, 111(6):1202-1206.

Fedi, Paolo et al., "Isolation and Biochemical Characterization of the Human Dkk-1 Homologue, a Novel Inhibitor of Mammalian Wnt Signaling," The Journal of Biological Chemistry, Jul. 1999, 274(27):19465-19472.

Felgner, P. L. et al., "Cationic liposome-mediated transfection," Nature, Jan. 1989, 337:387-388.

Filali, Mohammed et al., "Wnt-3A/β-Catenin Signaling Induces Transcription from the *LEF-1* Promoter," The Journal of Biological Chemistry, Sep. 2002, 277(36):33398-33410.

Finch, Paul W. et al., "Purification and Molecular cloning of a secreted, Frizzled-related antagonist of Wnt action," Proceedings of the National Academy of Sciences USA, Jun. 1997, 94:6770-6775.

Florenes, VA et al., "TGF-β mediated $G_1$ arrest in a human melanoma cell line lacking p15$^{INK4B}$: evidence for cooperation between p21$^{Cip1/WAF1}$ and P27$^{Kip1}$," Oncogene, 1996, 13:2447-2457.

Galderisi, Umberto et al., "Cell cycle regulation and neural differentiation," Oncogene, 2003, 22:5208-5219.

Gautier, Claudie et al., "α-DNA IV: α-anomeric and β-anomeric tetrathymidylates covalently linked to intercalating oxazolopryidocarbazole. Synthesis, physiochemical properties and poly (rA) binding," Nucleic Acids Research, 1987, 15(16):6625-6641.

Giles, Rachel H. et al., "Caught up in a Wnt storm: Wnt signaling in cancer," Biochimica et Biophysica Acta, 2003, 1653:1-24.

Glinka, Andrei et al., "Dickkopf-1 is a member of a new family of secreted proteins and functions in head induction," Nature, Jan. 1998, 391:357-362.

Going, J. J., "Stages on the way to breast cancer," Journal of Pathology, 2003, 199:1-3.

Greenblatt, M. S. et al., "Detailed computational study of *p53* and *p16*: using evolutionary sequence analysis and disease-associated mutations to predict the functional consequences of allelic variants," Oncogene, 2003, 22:1150-1163.

Gutierrez, Crisanto et al., "$G_1$ to S transition: more than a cell cycle engine switch," Current Opinion in Plant Biology, 2002, 5:480-486.

Hannon, Gregory J., "RNA interference," Nature, Jul. 2002, 418:244-251.

Harland, Mark et al., "Germline mutations of the CDKN2 gene in UK melanoma families," Human Molecular Genetics, 1997, 6(12):2061-2067.

Hawiger, Jacek, "Noninvasive intracellular delivery of functional peptides and proteins," Current Opinion in Chemical Biology, 1999, 3:89-94.

He, Tong-Chuan et al., "Identification of c-*MYC* as a Target of the APC Pathway," Science, Sep. 1998, 281:1509-1512.

Hendrix, Mary J. C., et al., "Molecular plasticity of human melanoma cells," Oncogene, 2003, 22:3070-3075.

Hofbauer, Gunther F. L., "Tyrosinase immunoreacitivty in formalin-fixed, paraffin-embedded primary and metastatic melanoma: frequency and distribution," Journal of Cutaneous Pathology, 1998, 25:204-209.

Hudziak, Robert M., et al., "p185*HER2* Monoclonal Antibody Has Antiproliferative Effects In Vitro and Sensitizes Human Breast Tumor Cells to Tumor Necrosis Factor," Molecular and Cellular Biology, Mar. 1989, 9(3):1165-1172.

Johnstone, Ricky E. et al., "Apoptosis: A Link between Cancer Genetics and Chemotherapy," Cell, Jan. 2002, 108:153-164.

Kim, Dong-Seok et al., "Transforming growth factor-β1 decreases melanin synthesis via delayed extracellular signal-regulated kinase activation," The International Journal of Biochemistry, 2004, 36:1482-1491.

Koller, Beverly H. et al., "Inactivating the β$_2$-microglobulin locus in mouse embryonic stem cells by homologous recombination," Proceedings of the National Academy of Sciences USA, Nov. 1989, 86:8932-8935.

Kubo, Akihito et al., "The p16 Status of Tumor Cell Lines Identifies Small Molecular Inhibitors Specific for Cyclin-dependent Kinase 4$^1$," Clinical Cancer Research, Dec. 1999, 5:4279-4286.

(56) References Cited

OTHER PUBLICATIONS

Kuhnert, Frank et al., "Essential requirement for Wnt signaling in proliferation of adult small intestine and colon revealed by adenoviral expression of Dickkopf-1," Proceedings of the National Academy of Sciences USA, Jan. 2004, 101(1): 266-271.

Lang, Pearon G., "Current Concepts in the Management of Patients with Melanoma," American Journal of Clinical Dermatology, 2002, 3(6):401-426.

Lazarov, Mirella et al., "CDK4 coexpression with Ras generates malignant human epidermal tumorigenesis," Nature Medicine, Oct. 2002, 8(10):1105-1114.

Leyns, Luc et al., "Frzb-1 Is a Secreted Antagonist of Wnt Signaling Expressed in the Spemann Organizer," Cell, Mar. 1997, 88:747-756.

Li, Yan et al., "Systematic Chemotherapy for the Treatment of Metastatic Melanoma," Seminars in Oncology, Oct. 2002, 29(5):413-426.

Li, Yi et al., "Evidence that transgenes encoding components of the Wnt signaling pathway preferentially induce mammary cancers from progenitor cells," Proceedings of the National Academy of Sciences USA, Dec. 2003, 100(26):15853-15858.

Lin, Keming et al., "The cysteine-rich frizzled domain of Frzb-1 is required and sufficient for modulation of Wnt signaling," Proceedings of National Academy Sciences USA, Oct. 1997, 94:11196-11200.

Liu, Bob Y. et al., "The transforming activity of Wnt effectors correlates with their ability to induce the accumulation of mammary progenitor cells," Proceedings of the National Academy of Sciences USA, Mar. 2004, 101(12):4158-4163.

Liu, Guizhong et al., "A Novel Mechanism for Wnt Activation of Canonical Signaling through the LRP6 Receptor," Molecular and Cellular Biology, Aug. 2003, 23(16):5825-5835.

Longo, Kenneth A., "Wnt Signaling Protects 3T3-L1 Preadipocytes from Apoptosis through Induction of Insulin-like Growth Factors," The Journal of Biological Chemistry, Oct. 2002, 277(41):38239-38244.

Macip, Salvador et al., "Influence of Induced Reactive Oxygen Species in p53-Mediated Cell Fate Decisions," Molecular and Cellular Biology, Dec. 2003, 23(23):8576-8585.

Macip, Salvador et al., "Inhibition of p21-mediated ROS accumulation can rescue p21-induced senescence," The EMBO Journal, 2002, 21(9):2180-2188.

Mandic, A. et al., "The MEK1 inhibitor PD98059 sensitizes C8161 melanoma cells to cisplatin-induced apoptosis," Melanoma Research, 2001, 11:11-19.

Mao, Bingyu et al. "Kremen proteins are Dickkopf receptors that regulate Wnt/β-catenin signaling," Nature, Jun. 2002, 417(6):664-667.

Mao, Bingyu et al., "LDL-receptor-related protein 6 is a receptor for Dickkopf proteins," Nature, May 2001, 411:321-325.

McManus, Michael, T. et al., "Gene silencing using micro-RNA designed hairpins," RNA, 2002, 8:842-850.

Merighi, Stefania et al., "Pyrazolotriazolopyrimidine derivatives sensitive melanoma cells to the chemotherapic drugs: taxol and vindesine," Biochemical Pharmacology, 2003, 66:739-748.

Mi, Zhibao et al., "Characterization of a Class of Cationic Peptides Able to Facilitate Efficient Protein Transduction in Vitro and in Vivo," Molecular Therapy, Oct. 2000, 2(4):339-347.

Morin, Patrice, J. et al. "Activation of β-Catenin-Tcf Signaling in Colon Cancer by Mutations in β-Catenin or APC," Science, Mar. 1997, 275:1787-1790.

Muzeau, Francoise et al., "Loss of Heterozygosity on Chromosome 9 and *p*16 (MTS1, CDKN2) Gene Mutations in Esophageal Cancers," International Journal of Cancer, 1997, 72:27-30.

Myers, C., et al. "Suramin: a novel growth factor antagonist with activity in hormone-refractory metastatic prostate cancer," Journal of Clinical Oncology, Jun. 1992, 10(6): Title page, 881-889.

Niehrs, Christof, "Head in the WNT: the molecular nature of Spemann's head organizer," Trends In Genetics, Aug. 1999, 15(8):314-319.

Noordermeer, Jasprien et al. "*dishevelled* and *armadillo* act in the Wingless signalling pathway in *Drosophila*," Nature, Jan. 1994, 367:80-83.

Nusse, Roel et al., "*Wnt* Genes," Cell, Jun. 1992, 69:1073-1087.

Okada, Hitoshi et al., "Pathways of Apoptotic and Non-Apoptotic Death in Tumour Cells," Nature Reviews: Cancer, Aug. 2004, 4:592-603.

Orford, Keith et al., "Exogenous Expression of β-Catenin Regulates Contact Inhibition, Anchorage-independent Growth, Anoikis, and Radiation-induced Cell Cycle Arrest," The Journal of Cell Biology, Aug. 1999, 146(4):855-867.

Ortega, Sagrario, et al., "Cyclin D-dependent kinases, INK4 inhibitors and cancer," Biochimica et Biophysica Acta, 2002, 1602:73-87.

Parrish, Susan et al., "Functional Anatomy of a dsRNA Trigger: Differential Requirement for the Two Trigger Strands in RNA Interference," Molecular Cell, Nov. 2000, 6:1077-1087.

Paul, Cynthia P. et al., "Effective expression of small interfering RNA in human cells," Nature Biotechnology, May 2002, 20:505-508.

Pavey, Sandra et al., "Microarray expression profiling in melanoma reveals a *BRAF* mutation signature," Oncogene, Mar. 2004, 23:4060-4067.

Piccolo, Stefano et al., "The head inducer Cerberus is a multifunctional antagonist of Nodal, BMP and Wnt signals," Nature, Feb. 1999, 397:707-710.

Pierce, Jacalyn H. et al., "Oncogenic Potential of *erb*B-2 in human mammary epithelial cells," Oncogene, 1991, 6:1189-1194.

Pinson, Kathleen I. et al., "An LDL-receptor-related protein mediates Wnt signalling in mice," Nature, Sep. 2000, 407:535-538.

Pinto, Daniel et al., "Canonical Wnt signals are essential for homeostasis of the intestinal epithelium," Genes & Development, 2003, 17:1709-1713.

Polakis, Paul, "Wnt signaling and cancer," Genes & Development, 2000, 14:1837-1851.

Polesskaya, Anna et al., "Wnt Signaling Induces the Myogenic Specification of Resident CD45$^+$ Adult Stem Cells during Muscle Regeneration," Cell, Jun. 2003, 113:841-852.

Radu, Aurelian et al., "PTEN Induces Cell Cycle Arrest by Decreasing the Level and Nuclear Localization of Cyclin D1," Molecular and Cellular Biology, Sep. 2003, 23(17):6139-6149.

Rattner, Amir et al., "A family of secreted proteins contains homology to the cysteine-rich ligand-binding domain of frizzled receptors," Proceedings of the National Academy of Sciences USA, Apr. 1997, 94:2859-2863.

Reya, Tannishtha et al., "A role for Wnt signalling in self-renewal of haematopoietic stem cells," Nature, May 2003, 423:409-414.

Rieber, Mary Strasberg et al., "Suppression of Cyclin D1 But Not CDK4 Or Cyclin A With Induction of Melanoma Terminal Differentiation," Biochemical and Biophysical Research Communications, Nov. 1995, 216(1):422-427.

Rockman, Steven P. et al., "Id2 Is a Target of the β-Catenin/T Cell Factor Pathway in Colon Carcinoma," The Journal of Biological Chemistry, Nov. 2001, 276(48):45113-45119.

Rotolo, Sabrina et al., "Effects on proliferation and melanogenesis by inhibition of mutant *BRAF* and expression of wild-type *INK4A* in melanoma cells," The International Journal of Cancer, 2005, 115:164-169.

Rowlands, Tracey M. et al., "Dissecting the roles of β-catenin and cyclin D1 during mammary development and neoplasia," Proceedings of the National Academy of Sciences USA, Sep. 2003, 100(20):11400-11405.

Ruas, Margarida et al., "The p16$^{INK4a}$/CDKN2A tumor suppressor and its relatives," Biochimica et Biophysica Acta, 1998, 1378:F115-F177.

Scherer, F. et al., "Magnetofection: enhancing and targeting gene delivery by magnetic force in vitro and in vivo," Gene Therapy, 2002, 9:102-109.

Scherr, Michaela et al., "Gene Silencing Mediated by Small Interfering RNAs in Mammalian Cells," Current Medicinal Chemistry, 2003, 10:245-256.

Schmitt, Clemens, A., "Senescence, Apoptosis and Therapy—Cutting The Lifelines of Cancer," Nature Reviews Cancer, Apr. 2003, 3:286-295.

(56) References Cited

OTHER PUBLICATIONS

Schwarze, Steven R. et al., "In vivo protein transduction: intracellular delivery of biologically active proteins, compounds and DNA," Trends in Pharmacological Sciences, Feb. 2000, 21:45-48.

Sekine, Shigeki et al., "Target disruption of the mutant β-catenin gene in colon cancer cell line HCT116: preservation of its malignant phenotype," Oncogene, 2002, 21:5906-5911.

Sellers, William R. et al., "Stable binding to E2F is not required for the reinoblastoma protein to activate transcription, promote differentiation, and suppress tumor cell growth," Genes & Development, 1998, 12:95-106.

Semenov, Mikhail V. et al., "Head inducer Dickkopf-1 is a ligand for Wnt coreceptor LRP6," Current Biology, Jun. 2001, 11:951-961.

Sharp, Phillip A. et al., "Molecular Biology: RNA Interference," Science, Mar. 2000, 287(5462):2431-2434.

Shimizu, Hiroyuki et al., "Transformation by Wnt Family Proteins Correlates with Regulation of β-Catenin," Cell Growth & Differentiation, Dec. 1997, 8:1349-1358.

Shtutman, Michael et al., "The cyclin D1 gene is a target of the β-catenin/LEF-1 pathway," Proceedings of the National Academy of Sciences USA, May 1999, 96:5522-5527.

Siegfried, Esther et al., "Components of *wingless* signalling in *Drosophila*," Nature, Jan. 1994, 367:76-80.

Slamon, Dennis J. et al., "Use of Chemotherapy Plus a Monoclonal Antibody Against Her2 for Metastatic Breast Cancer That Overexpresses Her2," The New England Journal of Medicine, Mar. 2001, 344(11):783-792.

Staal, Frank J.T. et al., "Wnt signals are transmitted through N-terminally dephosphorylated β-catenin," EMBO Reports, 2002, 3(1):63-68.

Stingl, John et al., "Characterization of bipotent mammary epithelial progenitor cells in normal adult human breast tissue," Breast Cancer Research and Treatment, 2001, 67:93-109.

Sugrue, Mary M. et al., "Wild-type p53 triggers a rapid senescence program in human tumor cells lacking functional p53," Proceedings of the National Academy of Sciences USA, Sep. 1997, 94:9648-9653.

Sumrejkanchanakij, Piyamas et al., "Role of cyclin D1 cytoplasmic sequestration in the survival of postmitotic neurons," Oncogene, 2003, 22:8723-8730.

Suzuki, Hiromu et al., "A genomic screen for genes upregulated by demethylation and histone deacetylase inhibition in human colorectal cancer," Nature Genetics, Jun. 2002, 31:141-149.

Tada, Masazumi et al., "*Xwnt11* is a target of *Xenopus* Brachyury: regulation of gastrulation movements via Dishevelled, but not through the canonical Wnt pathway," Development, 2000, 127:2227-2238.

Tamai, Keiko et al., "LDL-receptor-related proteins in Wnt signal transduction," Nature, Sep. 2000, 407:530-535.

Tetsu, Osamu et al., "β-Catenin regulates expression of cyclin D1 in colon carcinoma cells," Nature, Apr. 1999, 398:422-426.

Tiscornia, Gustavo et al. "A general method for gene knockdown in mice by using lentiviral vectors expressing small interfering RNA," Proceedings of the National Academy of Sciences USA, Feb. 2003, 100(4):1844-1848.

van de Wetering, Marc et al., "Armadillo Coactivates Transcription Driven by the Product of the *Drosophila* Segment Polarity Gene *dTCF*," Cell, Mar. 1997, 88:789-799.

van de Wetering, Marc et al., "The β-Catenin/TCF-4 Complex Imposes a Crypt Progenitor Phenotype on Colorectal Cancer Cells," Cell, Oct. 2002, 111:241-250.

van de Wetering, Marc et al., "WNT Signaling and Lymphocyte Development," Cell, Apr. 2002, 109:S13-S19.

van Leeuwen, Frank et al. "Biological activity of soluble *wingless* protein in cultured *Drosophila* imaginal disc cells," Nature, Mar. 1994, 368:342-344.

van Noort, Mascha et al., "Wnt Signaling Controls the Phosphorylation Status of β-Catenin," The Journal of Biological Chemistry, May 2002, 277(20):17901-17905.

Wallingford, John B. et al., "Dishevelled controls cell polarity during *Xenopus* gastrulation," Nature, May 2000, 405:81-85.

Wang, Shouwen et al., "Frzb, a Secreted Protein Expressed in the Spemann Organizer, Binds and Inhibits Wnt-8," Cell, Mar. 1997, 88:757-766.

Wang, Yanshu et al. "A Large Family of Putative Transmembrane Receptors Homologous to the Product of the *Drosophila* Tissue Polarity Gene *frizzled*," The Journal of Biological Chemistry, Feb. 1996, 271(8):4468-4476.

Wehrli, Marcel et al., "*arrow* encodes an LDL-receptor-related protein essential for Wingless signalling," Nature, Sep. 2000, 407:527-530.

Widlund, Hans R. et al., "*Microphthalamia*-associated transcription factor: a critical regulator of pigment cell development and survival," Oncogene, 2003, 22:3035-3041.

Willert, Karl et al., "β-catenin: a key mediator of Wnt signaling," Current Opinion in Genetics & Development, 1998, 8:95-102.

Winklbauer, Rudolf et al., "Frizzled-7 signalling controls tissue separation during *Xenopus* gastrulation," Nature, Oct. 2001, 413:856-860.

Wolfel, Thomas et al., "A $p16^{INK4a}$-Insensitive CDK4 Mutant Targeted by Cytolytic T Lymphocytes in a Human Melanoma," Science, Sep. 1995, 269:1281-1284.

Wong, Gwendolyn T. et al., "Differential Transformation of Mammary Epithelial Cells by *Wnt* Genes," Molecular and Cellular Biology, Sep. 1994, 14:6278-6286.

You, Zongbing et al., "Wnt signaling promotes oncogenic transformation by inhibiting c-Myc-induced apoptosis," The Journal of Cell Biology, Apr. 2002, 157(3):429-440.

Yu, Qunyan et al., "Specific protection against breast cancers by cyclin D1 ablation," Nature, Jun. 2001, 411:1017-1021.

Zijlstra, Maarten et al., "Germ-line trasmission of a disrupted $β_2$-microglobulin gene produced by homologous recombination in embryonic stem cells," Nature, Nov. 1989, 342:435-438.

Zuo, Lin et al., "Germline mutations in the $p16^{INK4a}$ binding domain of CDK4 in familial melanoma," Nature Genetics, Jan. 1996, 12:97-99.

International Search Report and Written Opinion, mailed Jan. 5, 2007, for the International Patent Application PCT/US05/41531.

Kawano, Yosiaki and Kypta, Robert, "Secreted antagonists of the Wnt signalling pathway," Journal of Cell Science 116: 2627-2634 (2003).

Melkonyan, Hovsep S., et al., "SARPs: A family of secreted apoptosis-related proteins," Proc. Natl. Acad. Sci. USA (Dec. 1997), 94:13636-13641.

Akiri, G, et al., Wnt pathway aberrations including autocrine Wnt activation occur at high frequency in human non-small-cell lung carcinoma, Oncogene, 2009, 28, pp. 2163-2172.

Licchesi, Julien D.F., et al., Epigenetic alteration of Wnt pathway antagonists in progressive glandular neoplasia of the lung, Carcinogenesis, 2008, 29(5), pp. 895-904.

Kansara, Maya et al., Wnt inhibitory factor 1 is epigenetically silenced in human osteosarcoma, and targeted disruption accelerates osteosarcomagenesis in mice, The Journal of Clinical Investigation, 2009, 119(4), pp. 837-851.

Schlange T, et al., Autocrine WNT signaling contributes to breast cancer cell proliferation via the canonical WNT pathway and EGFR transactivation, Breast Cancer Research, 2007, 9(5):R63, pp. 1-15.

Schlosshaurer Peter W., et al., APC truncation and increased β-catenin levels in a human breast cancer cell line, Carcinogenesis, 2000, 21(7), pp. 1453-1456.

Shigemitsu K, et al., Genetic alteration of the beta-catenin gene (CTNNB1) in human lung cancer and malignant mesothelioma and identification of a new 3p21.3 homozygous deletion., Oncogene, 2001, 20(31), pp. 4249-4257.

Bang H. Hoang, et al., "Dickkopf 3 Inhibits Invasion and Motility of Saos-2 Osteosarcoma Cells by Modulating the Wnt-β-Catenin Pathway", Cancer Res, vol. 64, pp. 2734-2739 (2004).

Liang You, et al., "Inhibition of Wnt-1 Signaling Induces Apoptosis in β-Catenin-Deficient Mesothelioma Cells", Cancer Res, vol. 64, pp. 3474-3478 (2004).

* cited by examiner

A

B

C

D

E

COMPOSITIONS AND METHODS FOR ALTERING WNT AUTOCRINE SIGNALING

This application is a 371 National Phase of International Application No. PCT/US05/041531, filed Nov. 15, 2005, which claims priority from U.S. Provisional Application Ser. No. 60/627,977, filed Nov. 15, 2004. Both applications are hereby incorporated by reference in their entirety.

TECHNICAL FIELD

The present disclosure generally relates to treating or preventing hyperproliferative diseases, and more specifically to compounds and methods for treating or preventing malignant neoplasms having increased Wnt signaling by altering such signaling with Wnt antagonists, Wnt receptor antagonists, or a combination thereof.

BACKGROUND

Wnt signaling plays a critical role in cell fate determination and tissue development (Nusse, R. and Varmus, H. E. (1992) Cell 69, 1073-1087; Cadigan, K. M., and Nusse, R. (1997) Genes Dev 11, 3286-3305). Certain members of this family of secreted glycoproteins interact with co-receptors, frizzled and LRP5/6, leading to inhibition of β-catenin phosphorylation by the serine threonine kinase, glycogen synthase kinase-β(GSK-3β) within a large cytoplasmic complex including Dishevelled (Dsh), APC and Axin (Giles, R. H., van Es, J. H., and Clevers, H. (2003) Biochim Biophys Acta 1653, 1-24). Inhibition of β-catenin phosphorylation impairs its degradation by the ubiquitin/proteasome pathway, resulting in accumulation of the uncomplexed cytosolic molecule. Uncomplexed β-catenin then translocates to the nucleus where it interacts with TCF/LEF, and activates target genes (Giles, R. H., van Es, J. H., and Clevers, H. (2003) Biochim Biophys Acta 1653, 1-24). Accumulating evidence indicates that signaling through the Wnt canonical pathway regulates the differentiation of adult stem cells in the epithelium of the colon (van de Wetering, M., de Lau, W., and Clevers, H. (2002) Cell 109 Suppl, S13-19) and skin (Alonso, L., and Fuchs, E. (2003) Genes Dev 17, 1189-1200), as well as in muscle (Polesskaya, A., Seale, P., and Rudnicki, M. A. (2003) Cell 113, 841-852) and hematopoietic cells (Reya, T., Duncan, A. W., Ailles, L., Domen, J., Scherer, D. C., Willert, K., Hintz, L., Nusse, R., and Weissman, I. L. (2003) Nature 423, 409-414). Constitutively activated Wnt signaling has also been shown to be causally involved in cancer (Polakis, P. (2000) Genes Dev 14, 1837-1851).

Extra-cellular inhibitors that function to fine-tune the spatial and temporal patterns of Wnt activity and act at the cell surface to inhibit Wnt signaling through its receptors have recently been discovered (Kawano, Y., and Kypta, R. (2003) J Cell Sci 116, 2627-2634). One group of Wnt antagonists is the secreted Frizzled Related Proteins (FRPs), which share sequence similarity with the Frizzled receptor CRD (cysteine rich domain), but lack the transmembrane and intracellular domains (Leyns, L., Bouwmeester, T., Kim, S. H., Piccolo, S., and De Robertis, E. M. (1997) Cell 88, 747-756; Wang, S., Krinks, M., Lin, K., Luyten, F. P., and Moos, M., Jr. (1997) Cell 88, 757-766; Finch, P. W., He, X., Kelley, M. J., Uren, A., Schaudies, R. P., Popescu, N. C., Rudikoff, S., Aaronson, S. A., Varmus, H. E., and Rubin, J. S. (1997) Proc Natl Acad Sci USA 94, 6770-6775). Through its CRD, FRP exhibits the ability to bind Wnt, form dimers and heterodimerize with frizzled (Leyns, L., Bouwmeester, T., Kim, S. H., Piccolo, S., and De Robertis, E. M. (1997) Cell 88, 747-756; Wang, S., Krinks, M., Lin, K., Luyten, F. P., and Moos, M., Jr. (1997) Cell 88, 757-766; Rattner, A., Hsieh, J. C., Smallwood, P. M., Gilbert, D. J., Copeland, N. G., Jenkins, N. A., and Nathans, J. (1997) Proc Natl Acad Sci USA 94, 2859-2863; Lin, K., Wang, S., Julius, M. A., Kitajewski, J., Moos, M., Jr., and Luyten, F. P. (1997) Proc Natl Acad Sci USA 94, 11196-11200; Bafico, A., Gazit, A., Pramila, T., Finch, P. W., Yaniv, A., and Aaronson, S. A. (1999) J Biol Chem 274, 16180-16187). Thus, FRP may act not only to sequester Wnts but also to inhibit Wnt signaling via formation of non-functional complexes with the frizzled receptor. Another Wnt antagonist is designated Dickkopf-1 (DKK1), which is the prototype of a family of secreted proteins structurally unrelated to Wnt or Frizzled (Glinka, A., Wu, W., Delius, H., Monaghan, A. P., Blumenstock, C., and Niehrs, C. (1998) Nature 391, 357-362; Fedi, P., Bafico, A., Nieto Soria, A., Burgess, W. H., Miki, T., Bottaro, D. P., Kraus, M. H., and Aaronson, S. A. (1999) J Biol Chem 274, 19465-19472). DKK1 binds the Wnt co-receptor LRP6 and causes its endocytosis through formation of a ternary complex with the transmembrane protein Kremen (Mao, B., Wu, W., Li, Y., Hoppe, D., Stannek, P., Glinka, A., and Niehrs, C. (2001) Nature 411, 321-325; Bafico, A., Liu, G., Yaniv, A., Gazit, A., and Aaronson, S. A. (2001) Nat Cell Biol 3, 683-686; Semenov, M. V., Tamai, K., Brott, B. K., Kuhl, M., Sokol, S., and He, X. (2001) Curr Biol 11, 951-961; Mao, B., Wu, W., Davidson, G., Marhold, J., Li, M., Mechler, B. M., Delius, H., Hoppe, D., Stannek, P., Walter, C., et al. (2002 Nature 417, 664-667).

Wnts were initially identified as a consequence of their transcriptional activation by mouse mammary tumor virus promoter insertion, which initiates mammary tumor formation (Nusse, R., and Varmus, H. E. (1992). Cell 69, 1073-1087). Later studies established that genetic alterations afflicting APC and β-catenin, leading to increased uncomplexed β-catenin levels, occur very commonly in human colon and other cancers (Polakis, P. (2000) Genes Dev 14, 1837-1851; Giles, R. H., van Es, J. H., and Clevers, H. (2003) Biochim Biophys Acta 1653, 1-24). Despite the initial discovery of a Wnt autocrine transforming mechanism in the mouse model more than two decades ago, evidence of this mechanism in human cancer is lacking.

There is a continuing need for the development of chemotherapeutic agents useful for treating or preventing cancer, or for use in combination with known cancer therapies. The present invention meets such needs, and further provides other related advantages.

BRIEF SUMMARY OF THE INVENTION

In one aspect, the present disclosure provides a method for inhibiting growth of a tumor cell, comprising contacting a tumor cell with a compound that alters Wnt signaling, said compound comprising a Wnt antagonist, a Wnt receptor antagonist, or a combination thereof. In certain embodiments, the compound that alters Wnt signaling is a polypeptide, an antisense RNA or an siRNA. In other embodiments, the compound that alters Wnt signaling is a Wnt antagonist, such as a secreted Frizzled-related protein or cerberus. In related embodiments, the compound that alters Wnt signaling is a Wnt receptor antagonist, which may be a polypeptide or fragment thereof, such as Dickkopf-1 (DKK1), or an siRNA, such as one specific for low density lipoprotein receptor-related protein (LRP) 5 or LRP6. In some embodiments of the methods provided herein, the compound that alters Wnt signaling can induce or enhance apoptosis. In certain embodiments, the method is used to treat specific tumor cells, such as ovarian cancer cells, breast cancer cells, non-small cell lung carcinomas, or colorectal cancer cells. In certain embodiments, the methods further comprise contacting the tumor cells with a chemotherapeutic agent or radiation. In some embodiments, the altered Wnt signaling is detected by measuring uncomplexed β-catenin levels. Any of the aforementioned compounds or combination of compounds is further formulated as a pharmaceutical composition comprising a pharmaceutically acceptable carrier or excipient.

In another aspect, the present disclosure provides an isolated LRP6 siRNA having a nucleotide sequence of 5'-CCG-CATGGTGATTGATGAA-3' (SEQ ID NO: 1). In certain embodiments, a complementary copy of the LRP siRNA is contained in an expression vector and is operably associated with an expression control sequence. In some embodiments, the expression vector has an expression control sequence that allows for expression in a tumor cell.

In still another aspect, the present disclosure provides a method for sensitizing a tumor to treatment, comprising contacting a tumor cell with a compound that alters Wnt signaling, said compound comprising a Wnt antagonist, a Wnt receptor antagonist, or a combination thereof. In certain embodiments, the compound that alters Wnt signaling is a polypeptide, an antisense RNA or an siRNA. In other embodiments, the compound that alters Wnt signaling is a Wnt antagonist, such as a secreted Frizzled-related protein or cerberus. In related embodiments, the compound that alters Wnt signaling is a Wnt receptor antagonist or is a protein, such as Dickkopf-1 (DKK1), or an siRNA, such as one specific for low density lipoprotein receptor-related protein (LRP) 5 or LRP6. In some embodiments of the methods provided herein, the compound that alters Wnt signaling can induce or enhance apoptosis. In certain embodiments, the method is used to treat specific tumor cells, such as ovarian cancer cells, breast cancer cells, non-small cell lung carcinomas, or colorectal cancer cells. In certain embodiments, the methods further comprise contacting the tumor cells with a chemotherapeutic agent or radiation. In some embodiments, the altered Wnt signaling is detected by measuring uncomplexed β-catenin levels. Any of the aforementioned compounds or combination of compounds is further formulated as a pharmaceutical composition comprising a pharmaceutically acceptable carrier or excipient.

These and other aspects of the present invention will become evident upon reference to the following detailed description and attached drawings. In addition, various references are set forth herein which describe in more detail certain procedures or compositions, and are therefore incorporated by reference in their entirety.

DETAILED DESCRIPTION OF THE INVENTION

Figure 1A:
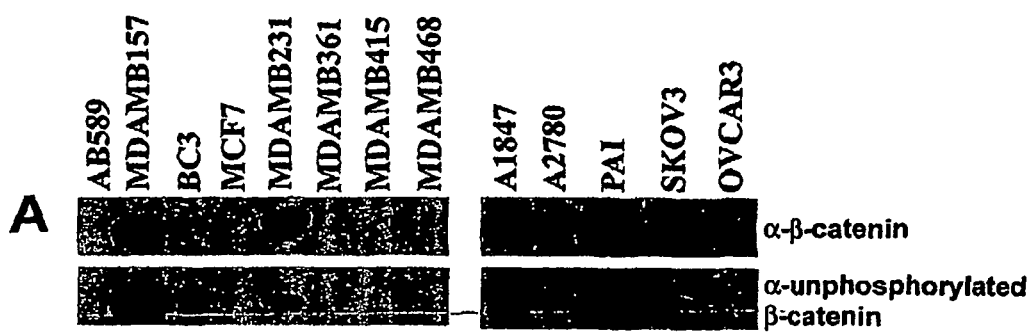
FIGS. 1A and 1B show up-regulation of Wnt signaling in the indicated human tumor breast and ovarian cancer cell lines. (A) Analysis of uncomplexed (upper panel) and unphosphorylated (lower panel) β-catenin protein levels in human tumor cells was performed with anti-β-catenin antibody. (B) RT-PCR analysis of levels of each indicated Wnt ligand, which was visualized by ethidium bromide staining.

The present invention provides an approach for inhibiting growth of tumor cells, and particularly for treating tumor cells in which the autocrine Wnt canonical signaling pathway is active. In particular, there are provided compositions and methods for altering Wnt signaling to inhibit tumor cell growth, to inhibit tumorgenicity, to sensitize a tumor cell to apoptosis, and to enhance or sensitize tumor cells to the anti-tumor activity of radiation therapy or chemotherapy.

More specifically, provided are Wnt antagonists and Wnt receptor antagonists. Thus, the invention advantageously provides a method for treating a mammal afflicted with a hyperproliferative disease (such as ovarian or breast cancer), in which the cells of the hyperproliferative disease have active Wnt signaling.

By way of background and not wishing to be bound by theory, frizzled (Fz) receptors are required in the Wnt signaling cascade for relaying signals inside the cell (Wang, Y., Macke, J. P., Abella, B. S., Andreasson, P. W., Gilbert, D. J., Copeland, N. G., Jenkins, N. A., and Nathans, J. (1996) J. Biol. Chem. 271, 4468-4476). The frizzled receptors have seven transmembrane domains and a cysteine-rich domain (CRD), which are involved in Wnt binding and signaling (Bhanot, P., Brink, M., Samos, C. H., Hsieh, J. C., Wang, Y., Macke, J. P., Andrew, D., Nathans, J. and Nusse, R. (1996) Nature 382, 225-230). Actually, Wnts have a heteroreceptor complex, in which LRP5/6 (Low-density-lipoprotein, LDL-receptor-related protein 5 and 6) act as a co-receptor (Tamai, K., Semenov, M., Kato, Y., Spokony, R., Liu, C., Katsuyama, Y., Hess, F., Saint-Jeannet, J. P., and He, X. (2000) Nature 407, 530-535). Wnt signalling can be inhibited by secreted frizzled-like proteins (sFRPs), which also have a CRD domain (Rattner, A., Hsieh, J. C., Smallwood, P. M., Gilbert, D. J., Copeland, N. G., Jenkins, N. A., and Nathans, J. (1997) Proc. Nat'l. Acad. Sci. U.S.A., 94, 2859-2863), by Dickkopf (Dkk) (Niehrs, C. (1999) Trends Genet. 15, 314-319) or Cerberus (Piccolo, S., Agius, E., Leyns, L., Bhattacharyya, S., Grunz, H., Bouwmeester, T. and De Robertis, E. M. (1999) Nature 397, 707-710). In cellular differentiation, at least three pathways exist for Wnt signaling: the canonical Wnt or disheveled-dependent β-catenin pathway, which contributes to the establishment of the dorsal-ventral axis (Willert, K. and Nusse, R. (1998) Curr. Opin. Genet. Dev. 8, 95-102), the planar cell polarity pathway, which is essential for cell polarization (Tada, M. and Smith, J. C. (2000) Development 127, 2227-2238; Wallingford, J. B., Rowning, B. A., Vogeli, K. M., Rothbacher, U., Fraser, S. E., and Harland, R. M. (2000) Nature 405, 81-85), and the disheveled-independent protein kinase C-pathway (Fz/PKC), which controls cell-sorting behavior in the mesoderm (Winklbauer, R., Medina, A., Swain, R. K., and Steinbeisser, H. (2001) Nature 413, 856-860).

In the canonical Wnt pathway, the signaling cascade is initiated at the cell membrane by interaction between the frizzled receptor and the Wnt protein. The signal is then transduced inside the cell to disheveled (Dsh) (Noordermeer, J., Klingensmith, J., Perrimon, N., and Nusse, R. (1994) Nature 367, 80-83), which becomes activated. This activation is followed by the inactivation of glycogen synthase kinase-3β (GSK-3β) (Siegfried, E., Wilder, E. L., and Perrimon, N. (1994) Nature 367, 76-80) leading to the accumulation of β-catenin in the cytoplasm (van Leeuwen, F., Samos, C. H., and Nusse, R. (1994) Nature 368, 342-344). β-catenin enters the nucleus and modulates gene expression together with TCFs (T-cell factors) (van de Wetering, M., Cavallo, R., Dooijes, D, van Beest, M., van Es, J., Loureiro, J., Ypma, A., Hursh, D., Jones, T. and Bejsovec, A. (1997) Cell 88, 789-799).

Any concentration, sequence, quantity, ratio or other numerical range recited herein is to be understood to include any integer within that range and fractions thereof, such as one tenth and one hundredth of an integer, unless otherwise indicated. It should be understood that indefinite terms, such as "a" and "an" as used above and elsewhere herein, refer to "one or more" of the enumerated components, and that the use of the alternative, such as "or," refers to each element individually, collectively or any combination thereof. As used herein, the term "about" means ±15% of an indicated value.

The invention provides various strategies for altering Wnt signaling, including use of polypeptides or peptides that antagonize Wnt proteins or Wnt receptors, use of nucleic acid sequences that encode polypeptides or peptides that antagonize Wnt proteins or Wnt receptors, and use of RNA interference (siRNA) or antisense olignucleotides that affect expression of Wnt proteins or Wnt receptors. In certain aspects, any of these approaches can be used therapeutically alone, in any combination thereof, or in combination with other therapeutics (e.g., inducers of apoptosis). The polypeptide or peptide-based approach involves delivering a polypeptide or peptide antagonist of Wnt proteins or Wnt receptors, or delivery of an anti-Wnt protein antibody or anti-Wnt receptor antibody to cells, each of which can alter Wnt signaling. A vector based approach involves delivering a vector comprising a gene encoding a compound that alters Wnt signaling, such as an antagonist of Wnt proteins or Wnt receptors, an anti-antagonist of Wnt protein antibody or anti-Wnt receptor antibody, or a Wnt protein or Wnt receptor siRNA or anti-sense nucleic acid sequence.

As used herein, the phrase "compound that alters Wnt signaling" refers to any polypeptide or peptide and fragments or derivatives thereof that antagonize Wnt signaling. Such compounds may be capable of associating directly with Wnt proteins or indirectly with the Wnt proteins via Wnt receptors or other associated proteins or molecules. In certain embodiments, the compound that alters Wnt signaling comprises a Wnt antagonist or overexpression of a Wnt antagonist, such as FRP or DKK1, including functional fragments and derivatives or analogues thereof (e.g., such as peptide fragments containing a CRD of FRP). In other embodiments, the compound that alters Wnt signaling comprises a Wnt protein domain that, for example, competitively inhibits binding of Wnt proteins to Wnt receptors. In still other embodiments, provided are siRNA specific for one or more Wnt receptors, such as frizzled, LRP5 or LRP6.

"Alteration of Wnt signaling" (and all grammatical variations thereof) includes inhibition of Wnt-dependent transcription as mediated by β-catenin. In certain embodiments, the alteration of Wnt signaling comprises inhibition of Wnt protein association with Wnt receptors, and inhibition of Wnt-dependent transcription, inhibition of tumor cell growth (relative to untreated tumor cells), an enhancement of spontaneous or inducible apoptosis, an increase in the sensitivity of tumor cells to therapy (particularly human ovarian, breast cancer and non-small cell lung carcinoma cells), such as UV radiation or treatment by chemotherapeutic drugs, and the like. In certain embodiments, inhibition of Wnt signaling inhibits growth of a tumor cell, which method further comprises inhibiting transcriptional activity of Wnt-dependent genes, such as Id2, Cyclin D1, and Myc. In still another embodiment, inhibition of Wnt activity comprises sensitizing a tumor cell to treatment with a chemotherapeutic or radiation or apoptosis, which method further comprises inhibiting the transcriptional activity of Wnt-dependent genes. As used herein, "sensitization" or "sensitizing a tumor cell" refers to increasing a cell's susceptibility to treatment, for example, by chemotherapy, radiation or entering a programmed cell death (apoptosis) pathway, including spontaneous (basal) or induced apoptoisis. In certain embodiments, the tumor cells being sensitized to neoplastic treatment or apoptosis are resistant to such treatment or signals.

As used herein, the term "tumor" refers to a malignant tissue comprising transformed cells that grow uncontrollably (i.e., is a hyperproliferative disease) and have active Wnt signaling. Tumors may include leukemias, lymphomas, myelomas, plasmacytomas, and the like; and solid tumors. Examples of solid tumors that can be treated according to the invention include sarcomas and carcinomas, such as: melanoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, head and neck carcinoma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma.

Monoclonal antibodies directed toward Wnt proteins, Wnt receptors, or fragments, analogs, or derivatives thereof, may be used. Methods of obtaining such antibodies include the hybridoma technique originally developed by Kohler and Milstein ((1975) *Nature* 256, 495-497), as well as the trioma technique, the human β-cell hybridoma technique (Kozbor et al. (1983) *Immunology Today* 4, 72; Cote et al. (1983) *Proc. Nat'l. Acad. Sci. U.S.A.* 80, 2026-2030), and the EBV-hybridoma technique to produce human monoclonal antibodies (Cole et al. (1985) in Monoclonal Antibodies and Cancer Therapy, Alan R. Liss, Inc., pp. 77-96). In an additional embodiment of the invention, monoclonal antibodies can be produced in germ-free animals (PCT Publication No. WO 89/12690). In fact, according to the invention, techniques developed for the production of "chimeric antibodies" (Morrison et al. (1984) *J. Bacteriol.* 159, 870; Neuberger et al. (1984) *Nature* 312, 604-608; and Takeda et al. (1985) *Nature* 314, 452-454) by splicing the genes from a mouse antibody molecule specific for a Wnt polypeptide or Wnt receptor polypeptide together with genes from a human antibody molecule of appropriate biological activity can be used; such antibodies are within the scope of this invention. Such human or humanized chimeric antibodies are preferred for use in therapy of human diseases or disorders (as described herein) because the human or humanized antibodies are much less likely than xenogenic antibodies to induce an immune response, in particular an allergic response, themselves.

According to the instant disclosure, techniques described for the production of single chain antibodies (U.S. Pat. Nos. 5,476,786 and 5,132,405 to Huston; U.S. Pat. No. 4,946,778) can be adapted to produce Wnt polypeptide- or Wnt receptor-specific single chain antibodies. Indeed, these genes can be delivered for expression in vivo. An additional embodiment of the invention utilizes the techniques described for the construction of Fab expression libraries (Huse et al. (1989) *Science* 246, 1275-1281) to allow rapid and easy identification of monoclonal Fab fragments with the desired specificity for a Wnt or Wnt receptor polypeptide, or its derivatives, or analogs. Single chain antibodies (which are the basis for most intrabody technology) are preferred, particularly those engineered to express a peptide translocation sequence.

Antibody fragments, which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic DNA and cDNA, RNA, any synthetic and genetically manipulated polynucleotide, and both sense and anti-sense polynucleotides (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "promoter" or "promoter sequence" is a DNA regulatory region capable of binding RNA polymerase in a cell and initiating transcription of a downstream (3' direction) coding sequence. For purposes of defining the present invention, a promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined), as well as protein binding domains (consensus sequences) responsible for the binding of RNA polymerase. The promoter may be operably associated with other expression control sequences, including enhancer and repressor sequences.

Promoters which may be used to control gene expression include, but are not limited to, elongation factor promoter from polyoma virus, cytomegalovirus (CMV) promoter (U.S. Pat. No. 5,385,839 and No. 5,168,062), the SV40 early promoter region (Benoist and Chambon (1981) *Nature,* 290, 304-310), the promoter contained in the 3' long terminal repeat of Rous sarcoma virus (Yamamoto et al. (1980) *Cell* 22, 787-797), the herpes thymidine kinase promoter (Wagner et al. (1981) *Proc. Natl. Acad. Sci. USA* 78, 1441-1445), the regulatory sequences of the metallothionein gene (Brinster et al. (1982) *Nature* 296, 39-42); prokaryotic expression vectors such as the beta-lactamase promoter (VIIIa-Komaroff et al. (1978) *Proc. Natl. Acad. Sci. U.S.A.* 75, 3727-3731), or the tac promoter (DeBoer et al. (1983) *Proc. Natl. Acad. Sci. U.S.A.* 80, 21-25); see also "Useful proteins from recombinant bacteria" in *Scientific American* (1980) 242:74-94; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Magram et al. (1985) *Nature* 315, 338-340; Kollias et al. (1986) *Cell* 46, 89-94), hematopoietic stem cell differentiation factor promoters, erythropoietin receptor promoter (Maouche et al. (1991) *Blood* 78, 2557-2563), etc. Inducible/repressible promoter systems can also be used, such as the tet, RU 486, and echdysone inducible systems, and the tet repressor system.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operably or operatively associated with" transcriptional and translational control sequences in a cell when RNA polymerase transcribes the coding sequence into RNA, particularly mRNA, which is then trans-RNA spliced (if it contains introns) and translated into the protein encoded by the coding sequence.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that can code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily be introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmids and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), pQE plasmids (Qiagen, Chatsworth, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, one or more tags or fusion sequences (such as a 6× histidine tag, HA tag or FLAG epitope), or one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

The term "expression system" means a host cell and compatible vector under suitable conditions, e.g. for the expression of a protein coded for by foreign DNA carried by the vector and introduced to the host cell. Common expression systems include $E.\ coli$ host cells and plasmid vectors, insect host cells and Baculovirus vectors, and mammalian host cells and vectors. In a specific embodiment, the protein of interest is expressed in COS-1 or $C_2C_{12}$ cells.

Other suitable cells include CHO cells, HeLa cells, 293T (human kidney cells), mouse primary myoblasts, and NIH 3T3 cells.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed, e.g., a CHO cell.

The terms "mutant" and "mutation" mean any detectable change in genetic material, e.g., DNA, or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al. (1987) Cell 50, 667). Such proteins (and their encoding genes) have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between nucleic acid or amino acid sequences of proteins that may or may not share a common evolutionary origin (see Reeck et al. (1987) Cell 50, 667). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15 M NaCl, 0.015 M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids encoding the protein. In a further embodiment, an oligonucleotide of the invention can form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

The present invention provides antisense nucleic acids (including ribozymes), which may be used to inhibit expression of a target protein of the invention. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a counter transcript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. Nos. 5,814,500; 5,811,234), or alternatively they can be prepared synthetically (e.g., U.S. Pat. No. 5,780,607).

Specific non-limiting examples of synthetic oligonucleotides envisioned for this invention include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—$PO_2$—O—$CH_2$). U.S. Pat. No. 5,677,437 describes heteroaromatic oligonucleoside linkages. Nitrogen linkers or groups containing nitrogen can also be used to prepare oligonucleotide mimics (U.S. Pat. No. 5,792,844 and No. 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen, P. E., Egholm, M., Berg, R. H., and Buchardt, O. (1991) Science 254, 1497-1500). Other synthetic oligonucleotides may contain substituted sugar moieties comprising one of the following at the 2' position: OH, SH, $SCH_3$, F, OCN, $O(CH_2)_nNNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

Preferred vectors in vitro, in vivo, and ex vivo are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in PCT Publication WO 95/28494.

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

In another embodiment, the vector can be non-viral. Such vectors include "naked" DNA, and transfection facilitating agents (peptides, polymers, etc.). Synthetic cationic lipids can be used to prepare liposomes for transfection of a gene encoding (Feigner et al. (1987) Proc. Nat'l. Acad. Sci. U.S.A. 84, 7413-7417; Felgner and Ringold (1989) Science 337, 387-388; see Mackey et al. (1988) Proc. Nat'l. Acad. Sci. U.S.A. 85, 8027-8031; Ulmer et al. (1993) Science 259, 1745-1748). Useful lipid compounds and compositions for transfer of nucleic acids are described in International Patent Publications WO95/18863 and WO96/17823, and in U.S. Pat. No. 5,459,127. Lipids may be chemically coupled to other molecules for the purpose of targeting (see Mackey et. al. (1988) Proc. Nat'l. Acad. Sci. U.S.A. 85, 8027-8031). Targeted peptides, e.g., hormones or neurotransmitters, and proteins such as antibodies, or non-peptide molecules could be coupled to liposomes chemically. Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al. (1992) J. Biol. Chem. 267, 963-967; Wu and Wu (1988) J. Biol. Chem. 263, 14621-14624; Hartmut et al., Canadian Patent Application No. 2,012,311, filed Mar. 15, 1990; and Williams et al. (1991) Proc. Nat'l. Acad. Sci. USA 88, 2726-2730). Receptor-mediated DNA delivery approaches can also be used (Curiel et al. (1992) Hum. Gene Ther. 3, 147-154; and Wu and Wu (1987) J. Biol. Chem. 262, 4429-4432). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al. (1998) C.P. Acad. Sci. 321, 893; WO 99/01157; WO 99/01158; and WO 99/01175).

Polypeptide or peptide compounds that alter Wnt signaling, as described herein, can be formulated in a pharmaceutical composition for administration to a patient. As used herein, a "pharmaceutical composition" includes the active agent, i.e., the peptide, fusion protein or vector, and a pharmaceutically acceptable carrier, excipient, or diluent. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal government or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water or oil, including those of petroleum, animal, vegetable or synthetic origin, such as peanut oil, soybean oil, mineral oil, sesame oil and the like. Water or aqueous solutions, saline solutions and aqueous dextrose and glycerol solutions are preferably employed as carriers, particularly for injectable solutions. Suitable pharmaceutical carriers are described in "Remington's Pharmaceutical Sciences" by E. W. Martin.

For human therapy, the pharmaceutical compositions, including each of the active agents, will be prepared in accordance with good manufacturing process (GMP) standards, as set by the Food & Drug Administration (FDA). Quality assurance (QA) and quality control (QC) standards will include testing for purity and function, in the case of polypeptides; homogeneity and function in the case of vectors; and the presence of replication competent virus (if the virus vector is defective) for viral vectors; and other standard measures.

In order to treat tumor cells, a pharmaceutical composition is administered by any route that will permit delivery of the active agent to a tumor cell. In certain embodiments, administration is parenteral, e.g., via intravenous injection, or by other routes, such as intra-arteriole, intramuscular, intradermal, subcutaneous, intraperitoneal, intraventricular, and intracranial administration. In other embodiments, delivery of a compound that alters Wnt signaling, such as a Wnt antagonist or a Wnt receptor antagonist, or compositions thereof, is delivered locally at the tumor, which can be topically or by injection into a tumor mass.

In therapeutic treatments of the invention, the physician will administer a therapeutically effective amount of the pharmaceutical composition. As used herein, the term "therapeutically effective amount" means an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. Specifically, a therapeutically effective amount will cause one or more of the following: apoptosis of tumor cells; necrosis of tumor cells; elimination or prevention of tumor metastases; reduction in the rate of tumor growth; reduction in tumor size or tumor shrinkage; elimination of the tumor; remission of the cancer; an increase in the time for reappearance of the cancer; and increased time of survival of the patient. The frequency and dosage of the therapy can be titrated by the ordinary physician using standard dose-to-response techniques.

The following summary discusses the results found in the Examples that follow, and should not limit the scope of the present invention.

The instant disclosure shows that constitutive up regulation of β-catenin in human tumor cells may occur by a novel mechanism involving Wnt autocrine signaling. This mechanism was initially discovered in the mouse mammary tumor model in which MMTV promoter insertion oncogenically activates Wnt expression (Nusse, R., and Varmus, H. E. (1992) Cell 69, 1073-1087), but was never followed up for over twenty years because M V does not infect human cells and it was unclear whether Wnt autocrine signaling would exist in human cells. Later studies identified mutations in downstream components of the Wnt signaling pathway resulting in up-regulation of this pathway in human colon carcinomas and a variety of other tumors (Polakis, P. (2000) Genes Dev 14, 1837-1851; Giles, R. H., van Es, J. H., and Clevers, H. (2003) Biochim Biophys Acta 1653, 1-24). The instant disclosure shows that several human breast and ovarian tumor cell lines, which were found to exhibit Wnt ligand expression and increased levels of the transcriptionally active form of unphosphorylated, uncomplexed β-catenin, surprisingly did not have detectable lesions in commonly implicated downstream signaling components, APC or β-catenin. FRP1 and DKK1, which are two exemplary antagonists of Wnt signaling at the level of ligand/receptor interactions (Leyns, L., Bouwmeester, T., Kim, S. H., Piccolo, S., and De Robertis, E. M. (1997) Cell 88, 747-756; Wang, S., Krinks, M., Lin, K., Luyten, F. P., and Moos, M., Jr. (1997) Cell 88, 757-766; Mao, B., Wu, W., Li, Y., Hoppe, D., Stannek, P., Glinka, A., and Niehrs, C. (2001) Nature 411, 321-325; Bafico, A., Liu, G., Yaniv, A., Gazit, A., and Aaronson, S. A. (2001) Nat Cell Biol 3, 683-686; Mao, B., Wu, W., Davidson, G., Marhold, J., Li, M., Mechler, B. M., Delius, H., Hoppe, D., Stannek, P., Walter, C., et al. (2002) Nature 417, 664-667), were shown in the instant disclosure to cause down regulation of uncomplexed β-catenin levels in tumor cells and strongly implicate an autocrine Wnt loop and a method of inhibiting the growth or increasing the sensitization of tumors.

In another exemplary embodiment, siRNAs directed against Wnt receptors LRP5 and LRP6 were used to alter autocrine Wnt signaling. The instant disclosure teaches that LRP6 was specifically responsible for transducing a Wnt autocrine signal in ovarian cancer cells. Moreover functional studies with a human breast tumor cells revealed that Wnt antagonists inhibited known Wnt-induced biological effects as well as Wnt target gene expression. The instant disclosure shows that autocrine Wnt signaling, as defined by the ability of the Wnt antagonists FRP1 and/or DKK1 to cause down regulation of activated β-catenin, was unexpectedly identified in about 25% of human breast and ovarian cancer cell lines analyzed, implicating this mechanism in a significant fraction of such tumors. All of these findings show that autocrine Wnt signaling can play a role in the etiology of human tumors, such as ovarian and breast cancer.

In representative Wnt autocrine tumor cells, it is demonstrated that soluble DKK1 caused a striking reduction in up regulated uncomplexed β-catenin to essentially undetectable levels, analogous to effects observed with Wnt transformed mouse cells. An increasing number of cancer agents have successfully targeted ligands or receptors at the cell surface (Hudziak, R. M., Lewis, G. D., Winget, M., Fendly, B. M., Shepard, H. M., and Ulirich, A. (1989) Mol Cell Biol 9, 1165-1172; Myers, C., Cooper, M., Stein, C., LaRocca, R., Walther, M. M., Weiss, G., Choyke, P., Dawson, N., Steinberg, S., Uhrich, M. M., and et al. (1992) J Clin Oncol 10, 881-889; Slamon, D. J., Leyland-Jones, B., Shak, S., Fuchs, H., Paton, V., Bajamonde, A., Fleming, T., Eiermann, W., Wolter, J., Pegram, M., et al. (2001) N Engl J Med 344, 783-792). Thus, a surprising result of the instant disclosure is that autocrine Wnt signaling can be targeted for therapeutic intervention with Wnt antagonists or Wnt receptor anatagonists or other modalities aimed at interfering with cell surface interactions involving Wnts and their receptors.

The present invention will be better understood by reference to the following Examples, which are provided by way of exemplification and not by way of limitation.

EXAMPLES

Example 1

DNA Constructs

Human FRP1 (Bafico et al., (1999) *J. Biol. Chem.* 274: 16180-16187) and DKK1 (Bafico et al., (2001) *Nat. Cell Biol.* 3:683-686) cDNAs were sub-cloned into a pBabe-derived retrovirus vector (Morgenstern and Land, (1990) Nucleic Acids Res. 18:3587-96) containing a carboxy-terminal HA tag and were co-transfected with the pCL-ampho packaging plasmid (Imgenex, Sorrento Valley, Calif.) into 293T cells (ATCC No. CRL-11268). Culture fluids were harvested at 72 hours and titrated on NIH3T3 cells (ATCC No. CRL-1658). The β-catenin cDNA, generously provided by Dr. W. Birchmeier (Hulsken et al., (1994) *J. Cell Biol.* 127:2061-2069), was expressed under the control of a Tet regulatable promoter using a system we have previously reported (Sugrue et al., (1997) *Proc. Nat'l Acad. Sci. U.S.A.* 94:9648-9653). pCMV-LRP6-Flag has been previously described (Liu et al., (2003) *Mol. Cell. Biol.* 23:5825-5835). Human LRP5, generously provided by Dr. Matthew Warman (Case Western Reserve University), was sub-cloned into pcDNA3.1 (Invitrogen).

Example 2

Cell Culture and Gene Transduction

Human tumor cell lines including breast (MDA-MB-157 (ATCC No. HTB-24), BC3 (ATCC No. CRL-2277), MCF7 (ATCC No. HTB-22), MDA-MB-231 (ATCC No. HTB-26), MDAMB134 (ATCC No. HTB-23), MDAMB175 (ATCC No. HTB-25), MDAMB435 (ATCC No. HTB-129), MDAMB453 (ATCC No. HTB-131), MDAMB361 (ATCC No. HTB-27), MDAMB415 (ATCC No. HTB-128), MDAMB468 (ATCC No. HTB-132)), ovarian (A1847, A2780, PAI, SKOV3 (ATCC No. HTB-77), OVCAR3 (ATCC No. HTB-161), 44S, 53S (ATCC No. HB-8182), 26S, OV90 (ATCC No. CRL-11732)) and colon HCT116 (ATCC No. CCL-247) were maintained in Dulbecco's modified Eagle's (DMEM) medium supplemented with 10% fetal bovine serum. The immortalized mammary epithelial cell line, AB589 (Stampfer and Bartley (1985) *Proc. Nat'l. Acad. Sci. U.S.A.* 82:2394-2398) was cultured in the same media with the addition of 1 µM dexamethasone (Sigma, St. Louis, Mo.). HCT116 allele-targeted clones engineered by homologous recombination have been described (Sekine, S., Shibata, T., Sakamoto, M., and Hirohashi, S. (2002) Oncogene 21, 5906-5911) and were maintained in DMEM containing 2 µg/ml puromycin (Calbiochem, San Diego, Calif.). NIH3T3 cells were maintained in DMEM medium supplemented with 10% calf serum. For retroviral mediated gene transduction cultures were plated at $5\times10^5$ cells per 60 mm plate in growth media containing 2 µg/ml of polybrene (Sigma, St. Louis, Mo.). Twenty four hours later cells were infected with vector control, FRP1 or DKK1 possessing either a puromycin or geneticin marker. Cells were selected for two weeks by addition of puromycin (0.5-2 µg/ml) or geneticin (750 µg/ml) (Invitrogen, Carlsbad, Calif.) to the growth media. In some cases, sub-confluent cultures were transfected using FuGene® (Roche, Indianapolis, Ind.) according to the manufacturer's instructions.

Example 3

GST-E-Cadherin Binding Assay and Immunoblot Analysis

β-catenin levels were assessed using the GST-E-cadherin binding assay, which has been previously described (Bafico et al., (1998) *Oncogene* 16:2819-2825). Briefly, bacterially expressed GST-E-cadherin was purified with glutathione-Sepharose beads and incubated with 1 mg of each cell lysate. The GST-E-cadherin/□-catenin complex bound to the beads was recovered by centrifugation and analyzed by SDS-PAGE followed by immunoblotting. The uncomplexed β-catenin was detected using a monoclonal antibody to β-catenin (Transduction Laboratories). Unphosphorylated β-catenin was detected with a monoclonal antibody specific for β-catenin dephosphorylated at residues 27-37 (Alexis, Läufelfingen, Switzerland). FRP1-HA and DKK1-HA were detected with an anti-HA monoclonal antibody (Hybridoma Center, Mount Sinai School of Medicine, New York).

Example 4

Identification of Human Breast and Ovarian Tumor Cell Lines with Constitutive Wnt Pathway Activation To search for evidence of autocrine Wnt signaling in human tumors, we initially surveyed a panel of human breast and ovarian tumor cell lines for increased levels of uncomplexed β-catenin. Human breast and ovarian tumor cell lines were cultured as described in Example 2. β-catenin levels were assessed using the GST-E-cadherin binding assay, which has been previously described (Bafico et al., (1998) *Oncogene* 16:2819-2825) (see Example 3). Briefly, bacterially expressed GST-E-cadherin was purified with glutathione-Sepharose beads and incubated with 1 mg of each cell lysate. The GST-E-cadherin/□-catenin complex bound to the beads was recovered by centrifugation and analyzed by SDS-PAGE followed by immunoblotting. The uncomplexed β-catenin was detected using a monoclonal antibody to β-catenin (Transduction Laboratories, Lexington, Ky.). Unphosphorylated β-catenin was detected with a monoclonal antibody specific for β-catenin dephosphorylated at residues 27-37 (Alexis).

Several human breast and ovarian tumor cell lines were identified as having increased levels of uncomplexed β-catenin (FIG. 1A and Table 1). Activation of Wnt signaling specifically increases the levels of N-terminally unphosphorylated β-catenin, which represents the transcriptionally active form of the protein (van Noort et al., (2002) *J. Biol. Chem.* 277:17901-17905; Staal et al., (2002) EMBO Rep. 3:63-68). Analysis of the uncomplexed β-catenin pool with an antibody that specifically recognizes the unphosphorylated form revealed that this pool in each case contained the transcriptionally active form (FIG. 1A). No detectable oncogenic lesions in either β-catenin or APC, the most frequently altered cancer genes in this pathway (Polakis (2000) *Genes Dev.* 14:1837-1851; Bienz and Clevers (2000) *Cell* 103:311-320), were found in any of these β-catenin upregulated tumor lines (data not shown), suggesting a novel mechanism.

Figure 1B:

In an effort to implicate Wnt autocrine signaling, we analyzed expression of representative Wnts by RT-PCR using primers specific for each. Total RNAs were extracted using Triazol (Invitrogen) and were reverse transcribed using the Superscript II Reverse Trancriptase (Invitrogen). 10 µl of a 100 µl cDNA reaction were utilized as template for amplification with the following primers specific for each Wnt. For human Wnt-2 forward: 5'-TGGCTCCCTCTGCTCT-TGACC-3' (SEQ ID NO: 2), and reverse: 5'-AGTCAATGT-TATCACTGCAGC-3' (SEQ ID NO: 3); for human Wnt-3 forward: 5'-GAAGGCTGGAAGTGGGGCGGCT-3' (SEQ ID NO: 4) and reverse: 5'-GTCTCCACCCAGCCTCGG-GACTCA-3' (SEQ ID NO: 5); for human Wnt-3a forward: 5'-GGATACTTCTTACTCCTCTGCAG-3' (SEQ ID NO: 6) and reverse: 5'-AATGGCGTGGACAAAGGCCGACT-3' (SEQ ID NO: 7). Expression of other Wnt family members was analyzed utilizing the Human WNT gene family multi-gene-12 RT-PCR profiling kit (SuperArray). RT-PCR products were visualized by ethidium bromide staining. FIG. 1B shows that the Wnt ligands analyzed exhibited different patterns of expression, and that the tumor cell lines containing up-regulated β-catenin expressed one or more of these Wnts.

TABLE 1

Wnt Signaling Upregulation in Human Tumor Cell Lines

| Cell Line | Uncomplexed β-catenin Level | Inhibition by FRP and/or DKK |
|---|---|---|
| Breast | | |
| AB589 | − | ND |
| BC3 | + | + |
| MDAMB134 | − | ND |
| MDAMB157 | ++++ | + |
| MDAMB175 | − | ND |
| MDAMB231 | ++ | + |
| MDAMB361 | − | ND |
| MDAMB415 | − | ND |
| MDAMB435 | − | ND |
| MDAMB453 | − | ND |
| MDAMB468 | − | ND |
| MCF7 | − | ND |
| Ovarian | | |
| OVCAR3 | + | − |
| A1847 | ++ | + |
| A2780 | − | ND |
| SKOV3 | + | +/− |
| 44S | + | +/− |
| PA1 | ++++ | + |

TABLE 1-continued

Wnt Signaling Upregulation in Human Tumor Cell Lines

| Cell Line | Uncomplexed β-catenin Level | Inhibition by FRP and/or DKK |
|---|---|---|
| 26S | − | ND |
| 53S | +++ | − |

Human tumor cell lines without detectable APC or β-catenin mutations were analyzed for expression of uncomplexed β-catenin as described herein. Relative levels were approximated based on comparison between different lines analyzed at the same time (see FIG. 1). Inhibition by FRP1 and/or DKK1 was scored as positive based in the results of at least three independent experiments (ND = not determined). All cell lines are available either from the inventors or public depositories, as described herein.

Example 5

Wnt Antagonists Identify Autocrine Wnt Signaling in Human Tumor Cells

To directly address the possibility of an autocrine signaling loop in these cells, we took advantage of the FRP1 and DKK1 antagonists, which inhibit Wnt signaling at the level of ligand/receptor interactions (Leyns, L., Bouwmeester, T., Kim, S. H., Piccolo, S., and De Robertis, E. M. (1997) Cell 88, 747-756; Wang, S., Krinks, M., Lin, K., Luyten, F. P., and Moos, M., Jr. (1997) Cell 88, 757-766; Bafico, A., Gazit, A., Pramila, T., Finch, P. W., Yaniv, A., and Aaronson, S. A. (1999) J Biol Chem 274, 16180-16187; Bafico, A., Liu, G., Yaniv, A., Gazit, A., and Aaronson, S. A. (2001) Nat Cell Biol 3, 683-686; Mao, B., Wu, W., Li, Y., Hoppe, D., Stannek, P., Glinka, A., and Niehrs, C. (2001) Nature 411, 321-325; Semenov, M. V., Tamai, K., Brott, B. K., Kuhl, M., Sokol, S., and He, X. (2001) Curr Biol 11, 951-961). NIH3T3 cells expressing β-catenin under the control of the Tet inducible promoter were grown in the presence of differing amounts of tetracycline (Sigma, St. Louis, Mo.): lanes 1 and 2: 1 µg/ml; lanes 3 and 4: 7.5 ng/ml; lanes 5 and 6: 5 ng/ml (see FIG. 2A). Wnt-3a expressing NIH3T3 cells (lanes 7 and 8) were incubated with purified DKK1 (10 nM). The NIH3T3 cells described above were subjected to the GST-E-cadherin binding assay (described in Example 3), followed by SDS-PAGE and immunoblot analysis with anti-β-catenin antibody (Transduction Laboratories).

Figure 2A:
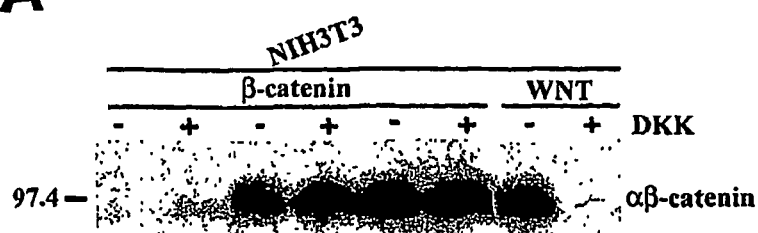
FIGS. 2A-2E show FRP1 and DKK1 inhibition of autocrine Wnt signaling in human tumor cell lines. (A) NIH3T3 cells expressing β-catenin under the control of the Tet inducible promoter (grown in the presence of differing amounts of tetracycline: lanes 1 and 2: 1 μg/ml; lanes 3 and 4: 7.5 ng/ml; lanes 5 and 6: 5 ng/ml), and Wnt-3a expressing NIH3T3 cells (lanes 7 and 8) were incubated with purified DKK1 (10 nM), subjected to the GST-E-cadherin binding assay, followed by SDS-PAGE and immunoblot analysis with anti-β-catenin antibody. (B) MDAMB 157 cell cultures were exposed to increasing concentration of purified DKK1, solubilized and analyzed for uncomplexed β-catenin as described in (A). (C) MDAMB157 cells were infected with vector alone, FRP1—HA or DKK1-HA retroviruses and marker selected (top panel), and expression of FRP1 (middle panel) and DKK1 (lower panel) were assessed by immunoblot analysis of lysates with an anti-HA antibody. (D) Breast (MDAMB231) and ovarian (A1847, PAI) tumor cell lines were analyzed for uncomplexed β-catenin (upper panel) or FRP1 and DKK1 (lower panel) by immunoblot analysis. (E) TCF responsive elements operably linked to a reporter (TOP-Glow, wild type, or FOP-Glow, mutant) were analyzed for transcriptional activity in PAI tumor cells in the presence or absence of DKK1.

As shown in FIG. 2A, addition of DKK1 to NIH3T3 cells stably expressing Wnt-3a resulted in striking inhibition of up-regulated β-catenin levels. In contrast, the same inhibitor had no effect on uncomplexed β-catenin induced by exogenous β-catenin expressed under the control of a tet regulatable promoter. Thus, if a Wnt autocrine loop were functional in human tumor cells, FRP1 or DKK1 antagonists should cause specific inhibition of up-regulated 13-catenin levels.

Figure 2B:
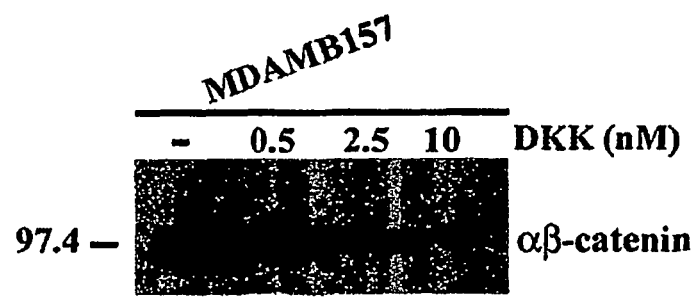

MDAMB157 cell cultures were exposed to increasing concentrations of purified DKK1, and then were solubilized and analyzed for uncomplexed β-catenin using immunoblot analysis and an anti-☐-catenin antibody as described in Example 3. As shown in FIG. 2B, exposure of MDAMB157 breast tumor cells to increasing concentrations (0.5-10 mM) of purified DKK1 (Bafico, A., Liu, G., Yaniv, A., Gazit, A., and Aaronson, S. A. (2001) Nat Cell Biol 3, 683-686), led to a dose dependent, marked reduction in the levels of uncomplexed β-catenin (FIG. 2B).

Figure 2C:
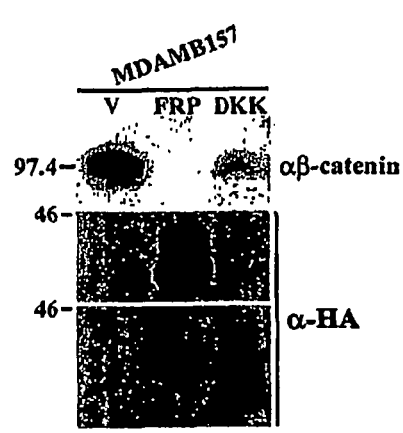

MDAMB157 cells were infected with vector alone, FRP1-HA (described in Example 1), or DKK1-HA (described in Example 1) retroviruses and marker selected. Uncomplexed β-catenin protein levels were analyzed using immunoblot analysis with an anti-β-catenin antibody as described in Example 3. Expression of FRP1-HA or DKK1-HA were assessed by immunblot analysis of lysates using an anti-HA monoclonal antibody (Hybridoma Center, Mount Sinai School of Medicine, New York). As illustrated in FIG. 2C, Stable expression of FRP 1 or DKK1 by retroviral mediated transduction in MDAMB157 cells led to a dramatic reduction in uncomplexed β-catenin levels as well.

Figure 2D:
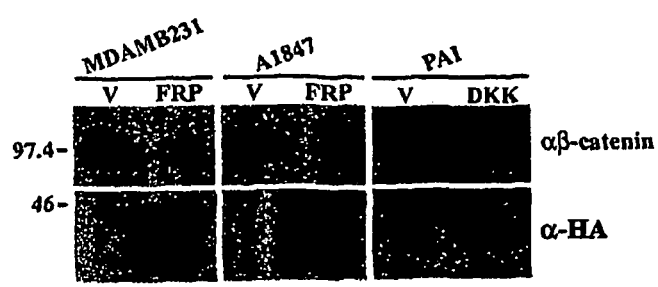

Breast (MDAMB231, ATCC No. HTB-26) and ovarian A1847 tumor cell lines were infected with vector alone or FRP 1-HA (described in Example 1) retroviruses and marker selected. Ovarian PAI tumor cell line was infected with vector alone or DKK1-HA (described in Example 1) retroviruses and marker selected. Breast (MDAMB231) and ovarian A1847 tumor cell lines were analyzed for uncomplexed β-catenin and FRP 1-HA by immunoblot analysis with either an anti-β-catenin antibody (Transduction Laboratories) or an anti-HA antibody (Hybridoma Center, Mount Sinai School of Medicine, New York). Ovarian PAI tumor cell line was analyzed for uncomplexed β-catenin and DKK1 by immunoblot analysis with either an anti-β-catenin antibody (Transduction Laboratories) or an anti-HA antibody (Hybridoma Center, Mount Sinai School of Medicine, New York). As shown in FIG. 2D, inhibition of constitutively up-regulated β-catenin was also observed with expression of FRP1 or DKK1 in several other breast and ovarian tumor cell lines including MDAMB231, A1847, and PAI.

Figure 2E:
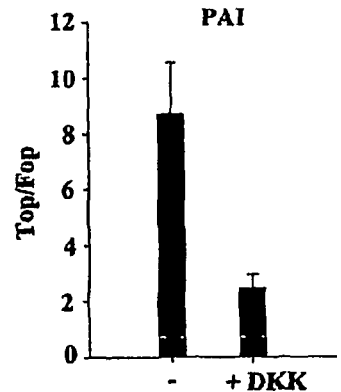

Wnt signaling activates TCF dependent transcription, which can be monitored by reporters containing TCF responsive elements (Morin et al., (1997) Science 275:1787-1790). TCF responsive elements operably linked to a reporter (TOP-Glow, wild type, or FOP-Glow, mutant) were analyzed for transcriptional activity in PAI tumor cells in the presence or absence of DKK1. Ovarian tumor PAI cells plated at $3\times10^5$ per well in 6-well plates were co-transfected with 1 µg of either the TOP-glow or FOP-glow plasmids (Upstate Biotechnology, Waltham, Mass.) and 0.001 µg of the Renilla control plasmid (pRL-CMV) utilizing Fugene (Roche) according to the manufacturer's instructions. After 48 hours cells were lysed and analyzed utilizing the Dual Luciferase Reporter Assay system (Promega, Madison, Wis.). As shown in FIG. 2E, DKK1 caused a striking reduction in the level of endogenous TCF dependent signaling in a representative ovarian tumor cell line, PAI. These findings further established that TCF dependent transcription was constitutively activated in these tumor cells by an autocrine Wnt mechanism.

As summarized in Table 1, three of eleven breast tumor cell lines exhibited up-regulated β-catenin, which in each case was inhibited by FRP1 and/or DKK1. Two of eight ovarian tumor cell lines demonstrated uncomplexed β-catenin levels, which were decreased in response to the antagonists. A high level of up-regulated β-catenin was detected in 53S tumor cells but showed no detectable response to the inhibitors, implying a lesion in the canonical pathway other than an autocrine loop.

Example 6

Figure 3A:
FIGS. 3A and 3B show up-regulation of Wnt signaling in human tumor breast cancer cell lines (FIG. 3A) and DKK1 inhibition of autocrine Wnt signaling in HCC38 breast cancer cells (FIG. 3B). (A) Analysis of uncomplexed β-catenin levels was performed using 1 mg of total cell lysate. A monoclonal antibody to β-catenin was used for immunoblotting. Lane 1 is from cell line HCC1806; Lane 2 is from cell line HCC1428; Lane 3 is from cell line HCC1143; Lane 4 is from cell line HCC38; and Lane 5 is from cell line HCC1395. (B) HCC38 breast cancer cell cultures were exposed to DKK containing conditioned media or media not containing DKK for two hours and then subjected to analysis of uncomplexed β-catenin levels using a monoclonal antibody to β-catenin.
Figure 3B:
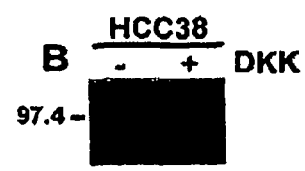

Identification of Human Breast Cancer Cell Lines with Constitutive Wnt Pathway Activation In addition, we have analyzed about 20 additional human breast cancer cell lines for increased levels of uncomplexed β-catenin. Analysis of uncomplexed β-catenin levels was performed as described in Example 3 utilizing 1 mg of total cell lysate. A monoclonal antibody to β-catenin (Transduction Laboratories) was utilized for immunoblotting. We found increased levels of uncomplexed β-catenin in 6 of these cell lines (FIG. 3A, lanes 1, 3, 4 and data not shown). We have also analyzed DKK inhibition of autocrine Wnt signaling in HCC38 breast cancer cells. Cultures were exposed to DKK1-containing conditioned media for two hours and subjected to analysis of uncomplexed β-catenin levels as described in Example 3 using a monoclonal antibody to β-catenin for immunoblotting (Transduction Laboratories). Several of the positive cell lines showed a striking reduction of uncomplexed β-catenin levels when exposed to DKK (FIG. 3B, and data not shown). These results further confirm and extend our findings of autocrine Wnt signaling as a novel mechanism for up-regulated β-catenin in a significant fraction of human breast carcinomas.

Example 7

Figure 4:
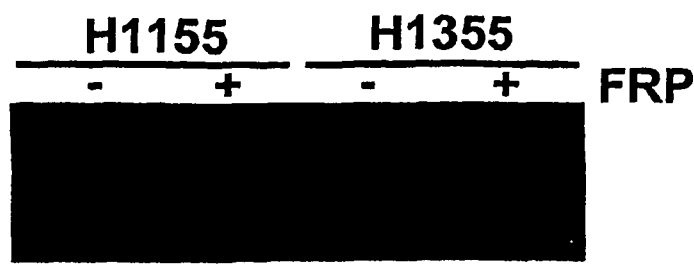
FIG. 4 shows FRP inhibition of autocrine Wnt signaling in non-small cell lung carcinomas (NSCLC) cancer cell lines. NSCLC cultures were infected with vector control or FRP retroviruses and the marker was selected. Analysis of uncomplexed β-catenin levels was performed using a monoclonal antibody to β-catenin.

Identification of Non-Small Cell Lung Carcinoma Cell Lines with Constitutive Wnt Pathway Activation We have investigated additional human tumor types for evidence of constitutive up-regulation of Wnt signaling. In a large series of tumor lines derived from non-small cell lung carcinomas (NSCLC), 8 of 22 lines analyzed showed increased levels of uncomplexed β-catenin. One of these lines contained a β-catenin activating mutation, but the others showed no detectable activating lesions (data not shown). Moreover, we did not find any evidence of APC inactivating mutations as determined by faster migration or lack of detection of the APC protein by SDS-PAGE and immunoblotting analysis with anti-APC (data not shown). We analyzed FRP inhibition of autocrine Wnt signaling in NSCLC cancer cell lines. Cultures were infected with vector control or FRP retroviruses (described in Example 1) and the marker was selected. Analysis of uncomplexed β-catenin levels was performed as described in Example 3 using a monoclonal antibody to β-catenin for immunoblotting. Exposure of some of these positive cell lines to FRP and/or DKK reduced the level of uncomplexed β-catenin (FIG. 4, and data not shown), providing evidence that a significant fraction of NSCLCs, like breast and ovarian carcinomas, possess constitutively activated autocrine Wnt signaling.

Example 8

Inhibition of Autocrine Wnt Signaling by siRNA Directed Against LRP6

In an effort to independently confirm the existence of an autocrine Wnt signaling loop, we generated siRNAs specific for LRP5 and LRP6, the Wnt co-receptors specific for the canonical pathway (Pinson et al., (2000) *Nature* 407:535-538) (Wehrli et al., (2000) *Nature* 407:527-530). siRNAs against RNA encoding the extracellular domain of human LRP5 and LRP6 were transiently expressed in 293T cells. siRNAs were constructed in the pSuper expression vector as previously described (Brummelkamp et al., (2002) *Science* 296:550-553). The 19-nucleotide target sequence for LRP6 was 5'-CCGCATGGTGATTGATGAA-3' (SEQ ID NO: 8), and for LRP5 was 5'-CATGATCGAGTCGTCCAAC-3' (SEQ ID NO: 9). 293 T or PAI cells were transiently transfected using Fugene (Roche) and analyzed after 72 hours.

Figure 5A:
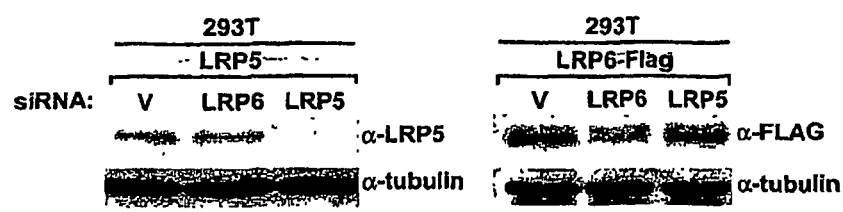
FIGS. 5A and 5B show the effects of LRP5 and LRP6 siRNAs on Wnt signaling. (A) siRNAs against RNA encoding the extracellular domain of human LRP5 and LRP6 were transiently expressed in 293T cells, and LRP5 and LRP6 protein levels were analyzed by immunoblot. (B) Effects of LRP5 and LRP6 siRNAs on Wnt-3a stimulated 293T cells or autocrine Wnt PAI human tumor cells was analyzed by immunoblot for uncomplexed β-catenin levels.
Figure 5B:
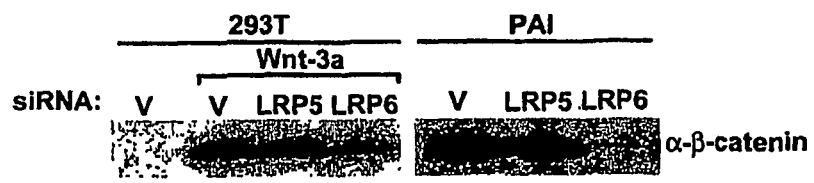

LRP5 and LRP6 protein levels were analyzed by immunoblot analysis using anti-LRP5 (Orbigen, San DIego, Calif.) or anti-FLAG (for LRP6-FLAG) antibodies (Sigma, St. Louis, Mo.). As shown in FIG. 5A, the exogenous expression of each LRP receptor in 293T cells was specifically inhibited by the homologous but not the heterologous siRNA. When the same siRNAs were expressed in 293T cells treated with Wnt-3a conditioned media, we observed that LRP6 siRNA caused a reduction in Wnt induced uncomplexed β-catenin levels, while LRP5 siRNA had no detectable effect (FIG. 5B, left panel). These results implied that canonical signaling in response to Wnt-3a in these cells required endogenous LRP6. There was no effect of either siRNA on uncomplexed β-catenin levels in 293T cells expressing mutant β-catenin under the same conditions (data not shown). We next tested the effects of these same siRNAs on PAI tumor cells and observed that LRP6 but not LRP5 siRNA caused a marked inhibition in uncomplexed β-catenin levels (FIG. 5B, right panel). These results provide strong evidence, independent of the use of Wnt antagonists, that constitutive Wnt signaling was due to an autocrine loop in these human tumor cells and implicated LRP6 as the specific Wnt canonical receptor involved.

Example 9

Effects of Wnt Autocrine Signaling Inhibition on Tumor Cell Phenotype

Exogenous expression of Wnts that signal through the canonical pathway in mammalian cells causes acquisition of properties associated with the transformed phenotype (Blasband, A., Schryver, B., and Papkoff, J. (1992) Oncogene 7, 153-161; Wong, G. T., Gavin, B. J., and McMahon, A. P. (1994) Mol Cell Biol 14, 6278-6286; Shimizu, H., Julius, M. A., Giarre, M., Zheng, Z., Brown, A. M., and Kitajewski, J. (1997) Cell Growth Differ 8, 1349-1358; Bafico, A., Gazit, A., Wu-Morgan, S. S., Yaniv, A., and Aaronson, S. A. (1998) Oncogene 16, 2819-2825; Orford, K., Orford, C. C., and Byers, S. W. (1999) J Cell Biol 146, 855-868). For example, stable expression of transforming Wnts in responsive cells induces increased saturation density, which can be specifically blocked by stable co-expression of FRP1 or DKK1 (Bafico, A., Gazit, A., Wu-Morgan, S. S., Yaniv, A., and Aaronson, S. A. (1998) Oncogene 16, 2819-2825; Fedi, P., Bafico, A., Nieto Soria, A., Burgess, W. H., Miki, T., Bottaro, D. P., Kraus, M. H., and Aaronson, S. A. (1999) J Biol Chem 274, 19465-19472). There is also evidence that Wnt signaling can inhibit apoptosis (Chen, S., Guttridge, D. C., You, Z., Zhang, Z., Fribley, A., Mayo, M. W., Kitajewski, J., and Wang, C. Y. (2001) J Cell Biol 152, 87-96; You, Z., Saims, D., Chen, S., Zhang, Z., Guttridge, D. C., Guan, K. L., MacDougald, O. A., Brown, A. M., Evan, G., Kitajewski, J., and Wang, C. Y. (2002) J Cell Biol 157, 429-440; Longo, K. A., Kennell, J. A., Ochocinska, M. J., Ross, S. E., Wright, W. S., and MacDougald, O. A. (2002) J Biol Chem 277, 38239-38244). Having identified human tumor cells with autocrine Wnt signaling, we analyzed the effects of FRP 1 or DKK 1 on these biological properties.

Figure 6A:
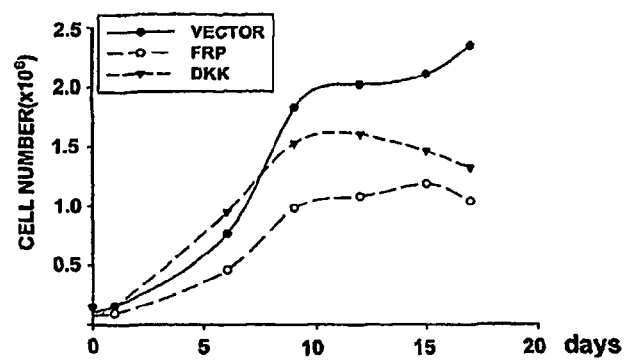
FIGS. 6A-6D show the functional effects of FRP1 and DKK1 inhibition of autocrine Wnt signaling in human breast tumor cells. (A) MDAMB157 cells exogenously expressing either vector control, FRP1 or DKK1 were transferred at $1.5 \times 10^5$ cells per well in 6-well plates. Cell counts were performed in duplicate at the indicated times, and values represent the mean of two independent experiments. (B) Sub-confluent cultures of MDAMB157 or AB589 were treated with the indicated amounts of tBh and subjected to FACS analysis to examine the effects of FRP1 and DKK1 on apoptosis in response to an oxidative stress inducer. The values obtained are expressed as the mean±standard deviation (s.d.) of two independent experiments performed in duplicate. (C) and (D) Total RNA extracted from MDAMB157 cells exogenously expressing vector alone, FRP1 or DKK1 were resolved on a 1% agarose gel and transferred to a nylon membrane to examine the effects of FRP1 and DKK1 on Wnt target genes and differentiation markers. Hybridization was performed with $\alpha$-$^{32}$P-dCTP labeled probes as indicated.

MDAMB157 cells exogenously expressing either vector control, FRP1 or DKK I were transferred at $1.5 \times 10^5$ cells per well in 6-well plates. Cell counts were performed in duplicate at the indicated times, and values represent the mean of two independent experiments. As shown in FIG. 6A, MDAMB157 cells over-expressing FRP1 or DKK1 exhibited decreased saturation density when compared to vector transduced parental cells.

To confirm that the effects of FRP1 and DKK1 on MDAMB 157 were through inhibition of Wnt function, we infected the immortalized human mammary epithelial cell line, AB589 (Stampfer, M. R., and Bartley, J. C. (1985) Proc Natl Acad Sci USA 82, 2394-2398), which exhibited undetectable levels of uncomplexed β-catenin (see FIG. 1A) with either vector, FRP1 or DKK1 retroviruses. Expression of the inhibitors in these cells resulted in no detectable effect on saturation density (data not shown).

To assess the effects of Wnt inhibition by FRP1 or DKK1 on the response of MDAMB157 cells to apoptotic stimuli, we exposed AB589 or MDAMB157 cells expressing either vector control, FRP1 or DKK1 to increasing concentrations of tert-butyl hydroperoxide (tBh) (Sigma) a known inducer of oxidative stress that causes DNA damage through reactive oxygen species (ROS) (Macip et al., (2003) *Mol. Cell. Biol.* 23:8576-8585), and analyzed the apoptotic response. Subconfluent cultures were treated with increasing amounts of tert-butyl hydroperoxide (tBH) for 2 hours. Twenty-four hours later, cells were washed in PBS, trypsinized and incubated with Annexin and PI using the Annexin-V-Fluos Staining kit (Roche). Fluorescent stained cells were subjected to FACS (Beckton Dickinson FACScan) using Cell Quest 3.2 software (Beckton Dickinson) for acquisition and analysis.

Figure 6B:
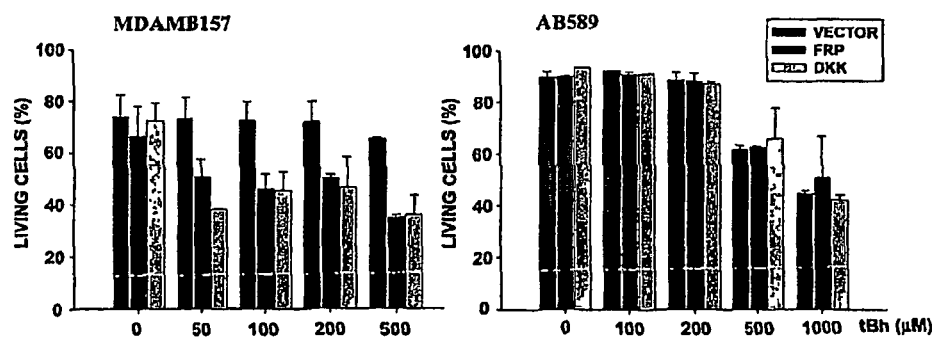

At each concentration of tBh analyzed, there was a statistically significant increase in the level of apoptosis in the presence of FRP1 or DKK1 over-expression in MDAMB157 cells (FIG. 6B, left panel). We have also tested the effects of tBh on lung tumor cells with autocrine Wnt signaling in the presence or absence of the Wnt antagonists FRP and DKK. As in the case of MDAMB157 (Bafico et al., (2004) *Cancer Cell* 6(5):497-506), H1355 (ATCC No. CRL-5865) non-small lung cell carcinoma (NSCLC) cells were more sensitive to induction of apoptosis by tBh when autocrine Wnt signaling was down-regulated (data not shown). Similar experiments performed with AB589 cells expressing FRP1 or DKK1 revealed no detectable differences in their apoptotic responses compared to the vector infected cells (FIG. 6B, right panel). These findings indicate that inhibition of a Wnt autocrine signaling mechanism in tumor cells by Wnt antagonists such as FRP or DKK would make them more sensitive to the killing effects of standard chemo or irradiation therapies. We noted that levels of expression of these antagonists decreased with passage of the transfected and marker selected tumor cells. This made it difficult to study their effects on tumor formation in vivo and suggested a negative selective pressure in tissue culture against these antagonists in Wnt autocrine tumor cells.

Alterations in the expression of a number of genes identified as targets of canonical Wnt signaling have been reported, although it should be noted that there is variability among Wnt target genes in different cell systems (Giles et al., (2003). *Biochim. Biophys. Acta* 1653:1-24). To investigate the effects of FRP1 and DKK1 inhibition on gene expression in MDAMB157 breast tumor cells, Northern blot analysis was performed on representative Wnt transcriptional targets, including Myc (He et al., (1998) *Science* 281:1509-1512), the LEF-1 transcription factor (Filali et al., (2002) *J. Biol. Chem.* 277:33398-33410) and the dominant negative helix-loop-helix transcriptional regulator, Id2 (Rockman et al., (2001) *J. Biol. Chem.* 276:45113-45119).

Total RNAs from MDAMB157 cells exogenously expressing vector alone, FRP1, or DKK1 were extracted using Triazol (Invitrogen), separated by agarose gel electrophoresis (1% agarose gel) and transferred to a nylon membrane (Hybond, Pharmacia). Probes were labeled by the Random Prime Labelling System method (Amersham Biosciences), and hybridization was performed overnight utilizing the Hybrisol I solution (Serologicals Corporation) according to the manufacturer's instructions. Normalization was performed utilizing a commercial human GADPH control probe (BD Biosciences Clontech). Probes were labelled with $\alpha$-$^{32}$P-dCTP.

Figure 6C:
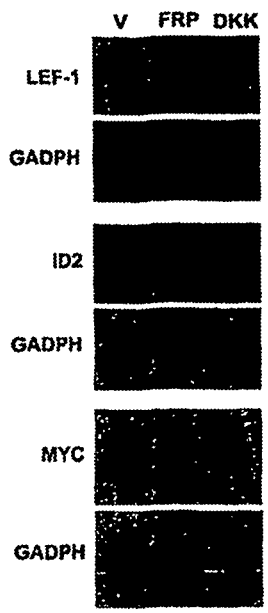

Of note, the expression of each (LEF-1, ID2, and MYC) was reduced by stable expression of FRP1 or DKK1 (FIG. 6C). We did not observe significant changes in the levels of another Wnt target gene, cyclin D1 (Tetsu and McCormick (1999) *Nature* 398, 422-426; Shtutman et al. (1999) *Proc Natl Acad Sci U.S.A.* 96, 5522-5527) under the same conditions (data not shown). However, it should be noted that Wnt can induce mammary tumors in the mouse in a cyclin D1 null genetic background implying that in this tissue at least, cyclin D1 is unlikely to be a critical Wnt target (Yu et al. (2001) *Nature* 411:1017-1021; Rowlands et al. (2003) *Proc Natl Acad Sci U.S.A.* 100:11400-11405).

Figure 6D:
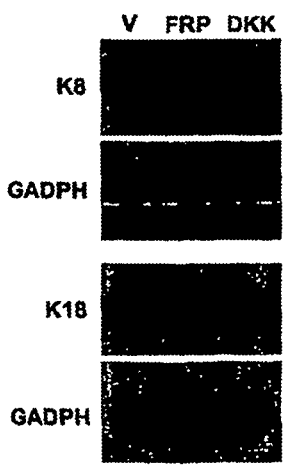

Since canonical Wnt signaling appears to be involved in maintaining epithelial progenitor cells of several tissues (van de Wetering et al. (2002) *Cell* 111:241-250; Alonso and Fuchs (2003) *Genes Dev.* 17:1189-1200; Reya et al. (2003) *Nature* 423:409-414; Polesskaya et al. (2003) *Cell* 113, 841-852), including the mouse mammary gland (Li et al. (2003) *Proc Natl Acad Sci U.S.A.* 100:15853-15858; Liu et al. (2004) *Proc. Nat'l Acad. Sci. U.S.A.* 101:4158-4163), we also investigated whether downregulation of Wnt signaling in MDAMB157 tumor cells affected their differentiated state. RNA blot analysis (as described above for LEF-1, ID2 and MYC) with probes for keratins 8 and 18, two markers known to be expressed by differentiated mammary epithelial cells (Stingl et al. (2001) *Breast Cancer Res. Treat.* 67:93-109; Going (2003) *J. Pathol.* 199:1-3; He et al. (1998) *Science* 281:1509-1512), revealed that stable expression of FRP1 or DKK1 led to a striking increase in the expression of keratin 8 as well as an increase in keratin 18 levels (FIG. 6D). All of these findings provide evidence for a Wnt autocrine transforming mechanism in human tumor cells.

Example 10

Effects of Wnt Antagonists on HCT116 Colon Cancer Cells with Knockout of Either Wild Type or Mutant $\beta$-Catenin Physiological Wnt signaling appears to be required for maintenance of the crypt progenitor phenotype in colonic epithelium (Pinto, D., Gregorieff, A., Begthel, H., and Clevers, H. (2003) Genes Dev 17, 1709-1713) (Kuhnert, F., Davis, C. R., Wang, H. T., Chu, P., Lee, M., Yuan, J., Nusse, R., and Kuo, C. J. (2004) Proc Natl Acad Sci USA 101, 266-271). Recent findings that FRP1 is mutated or methylated in a high fraction of colon carcinomas (Suzuki, H., Gabrielson, E., Chen, W., Anbazhagan, R., van Engeland, M., Weijenberg, M. P., Herman, J. G., and Baylin, S. B. (2002) Nat Genet. 31, 141-149) (Caldwell, G. M., Jones, C., Gensberg, K., Jan, S., Hardy, R. G., Byrd, P., Chughtai, S., Wallis, Y., Matthews, G. M., and Morton, D. G. (2004) Cancer Res 64, 883-888) led us to investigate whether a contribution of Wnt autocrine signaling in such tumors might be masked by mutations in downstream components of this pathway. For this purpose, we took advantage of the HCT116 colorectal cancer cell line, which harbors a $\beta$-catenin mutation (Morin, P. J., Sparks, A. B., Korinek, V., Barker, N., Clevers, H., Vogelstein, B., and Kinzler, K. W. (1997) Science 275, 1787-1790). HCT116 clones have been engineered by homologous recombination to contain either the wild type or mutant $\beta$-catenin allele (Sekine, S., Shibata, T., Sakamoto, M., and Hirohashi, S. (2002) Oncogene 21: 5906-5911; Chan, T. A., Wang, Z., Dang, L. H., Vogelstein, B., and Kinzler, K. W. (2002) Proc Natl Acad SCi USA 99: 8265-8270).

Figure 7A:
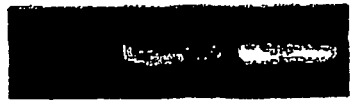
FIGS. 7A-7F show Wnt autocrine signaling in HCT116 human colon cancer cells. (A) RT-PCR was used to analyze expression of each indicated Wnt ligand in HCT116 colorectal cancer cell. (B) HCT116 parental cells and clones expressing either wt or mutant β-catenin allele were transfected with FRP1-HA and subjected to the GST-E-cadherin binding assay to examine the effect of FRP1 on uncomplexed β-catenin levels. Uncomplexed β-catenin was detected with anti-β-catenin antibody (upper panel). The levels of FRP1 in the lysates were detected with an anti-HA antibody (lower panels). (C) Top: Northern blot analysis of Id2. RNA extracted from HCT116 parental cells, and either wt or mutant β-catenin allele-containing clones transfected with either vector control or FRP 1-HA to examine the effect of FRP 1 on the Id2 target gene expression. Bottom: As controls for FRP1 function, cell lysates were obtained at the same time as the RNA extraction and analyzed as in (B). (D) Hybridization was performed utilizing $^{32}$Pα-dCTP labelled cDNAs for either Cyclin D1 or c-myc to examine the effect of FRP1 on Cyclin D1 and Myc gene expression. (E) Cells were transfected and analyzed as in FIG. 2E to examine the effect of FRP1 on TCF-reporter transcriptional activity. (F) The indicated cell lines were subcutaneously injected into nude mice at $2.5 \times 10^6$ per site to examine the effect of FRP on tumor formation. Tumor size was monitored weekly, and values represent the mean (± Standard Deviation (SD)) of 4 inoculation sites per cell line.

RT-PCR was used to analyze expression of Wnt-2, Wnt-3 and Wnt-3a ligands in HCT116 colorectal cancer cells. Total RNAs were extracted from HCT116 colorectal cancer cells using Triazol (Invitrogen) and were reverse transcribed using the Superscript II Reverse Trancriptase (Invitrogen). 101 µl of a 100 µl cDNA reaction were utilized as template for amplification with the following primers specific for each Wnt. For human Wnt-2 forward: 5'-TGGCTCCCTCTGCTCT-TGACC-3' (SEQ ID NO: 2), and reverse: 5'-AGTCAATGT-TATCACTGCAGC-3' (SEQ ID NO: 3); for human Wnt-3 forward: 5'-GAAGGCTGGAAGTGGGGCGGCT-3' (SEQ ID NO: 4) and reverse: 5'-GTCTCCACCCAGCCTCGG-GACTCA-3' (SEQ ID NO: 5); for human Wnt-3a forward: 5'-GGATACTTCTTACTCCTCTGCAG-3' (SEQ ID NO: 6) and reverse: 5'-AATGGCGTGGACAAAGGCCGACT-3' (SEQ ID NO: 7). RT-PCR products were visualized with ethidium bromide staining. RT-PCR analysis revealed expression of canonical Wnt ligands including the highly transforming Wnt-3a in HCT116 cells (FIG. 7A).

Figure 7B:
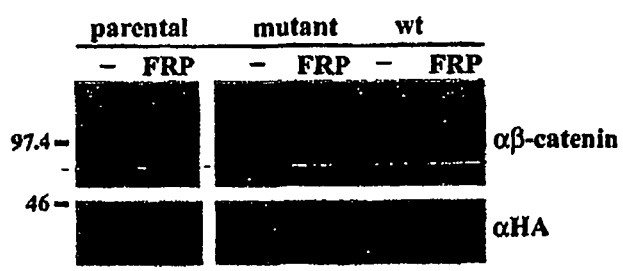
Figure 7C:
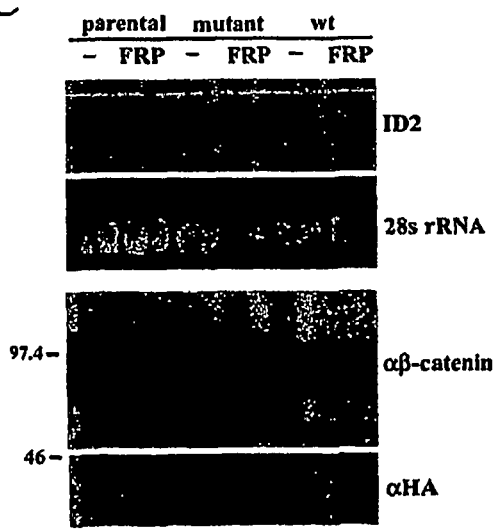

HCT116 parental cells and clones expressing either the wild type or mutant β-catenin allele were transfected with FRP1-HA and subjected to the GST-E-cadherin binding assay (described in Example 3) to examine the effect of FRP1 on uncomplexed β-catenin levels. Uncomplexed β-catenin was detected with anti-β-catenin antibody. The levels of FRP1 in the lysates were detected with an anti-HA antibody. The wt allele-containing clone retained high levels of uncomplexed β-catenin, indicating constitutive up-regulation of the Wnt pathway independent of the presence of the mutant β-catenin allele (FIG. 7B). Similar results were observed with other wt β-catenin allele containing clones (data not shown). Whereas FRP1 expression had little if any effect on uncomplexed β-catenin levels in the clone containing only the mutant allele, there was a dramatic reduction in β-catenin levels in the wild type β-catenin allele-containing clone (FIG. 7B). These findings established that an autocrine Wnt loop must exist in HCT116 cells.

Figure 7D:
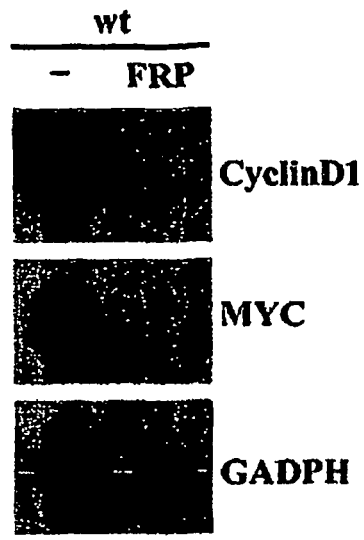

We next assessed the effects of FRP1 inhibition on the expression of Id2, Cyclin D1 and Myc, known targets of Wnt/β-catenin in colorectal cancer (Rockman et al. (2001) *J. Biol. Chem.* 276:45113-45119; Tetsu and McCormick (1999) *Nature* 398:422-426; He et al. (1998) *Science* 281:1509-1512). RNAs were extracted from HCT116 parental cells, and either wild type or mutant β-catenin allele containing clones transfected with either vector control or FRP1-HA using Triazol (Invitrogen). The RNAs were separated by (1%) agarose gel electrophoresis and transferred to a nylon membrane (Hybond®, Pharmacia). Probes were labeled by the Random Prime Labelling System method (Amersham Biosciences), and hybridization was performed overnight utilizing the Hybrisol I solution (Serologicals Corporation) according to the manufacturer's instructions. Normalization was performed utilizing a commercial human GADPH control probe (BD Biosciences Clontech). Northern blot analysis revealed high levels of Id2 expression in parental HCT116 as well as in the β-catenin mutant allele clone. The wild type β-catenin allele containing clone also showed Id2 expression at somewhat lower level, consistent with the relative levels of uncomplexed β-catenin observed in these clones (FIGS. 7B and C). Of note, FRP1 expression led to reduction in the Id2 transcript level in the wild type β-catenin but not in the mutant allele-containing clone. Similarly, expression of Cyclin D1 and Myc in the wild type allele-containing clone was dramatically inhibited by FRP1 expression (FIG. 7D).

Figure 7E:
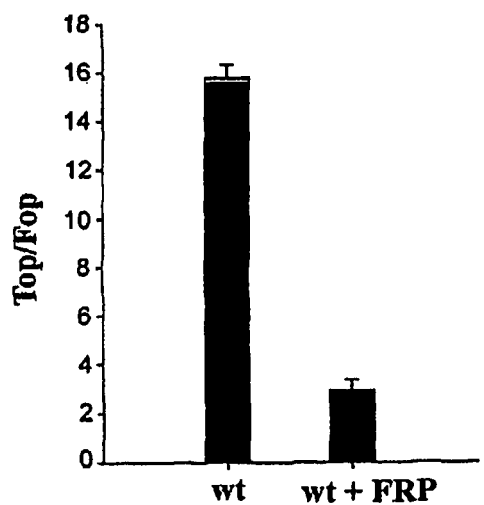

TCF responsive elements operably linked to a reporter (TOP-Glow, wild type, or FOP-Glow, mutant) were analyzed for transcriptional activity in PAI tumor cells in the presence or absence of DKK1. HCT116 (ATCC No. CCL-247) cells containing the wild type β-catenin allele were plated at $3 \times 10^5$ per well in 6-well plates and co-transfected with 1 μg of either the TOP-glow or FOP-glow plasmids (Upstate Biotechnology) and 0.001 μg of the *Renilla* control plasmid (pRL-CMV) utilizing FuGene® (Roche) according to the manufacturer's instructions. After 48 hours cells were lysed and analyzed utilizing the Dual Luciferase Reporter Assay system (Promega). As shown in FIG. 7E, FRP1 was able to inhibit TCF-dependent reporter activity in the β-catenin wild type allele clone (FIG. 7E).

Figure 7F:
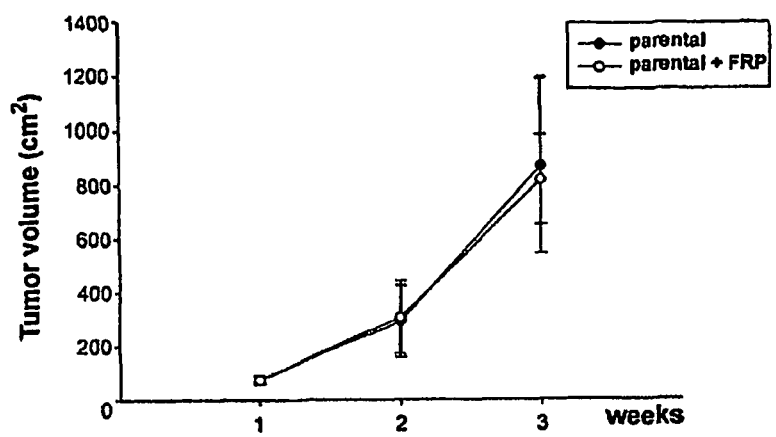

To assess the effects of Wnt autocrine inhibition in vivo, tumorigenicity experiments were performed utilizing parental or β-catenin wild type allele containing HCT116 cell lines, in which stable marker selected mass cultures expressing FRP1 were obtained. Parental and wild type β-catenin allele containing HCT116 cells were transfected with either vector control or FRP1. Marker selected mass cultures of each were subcutaneously injected in 6 week old nude mice at $2.5 \times 10^6$ cells per site. Tumor growth was monitored at weekly intervals as previously described (Pierce et al. (1991) *Oncogene* 6:1189-1194). Values in FIG. 7F represent the mean (± standard deviation) of 4 inoculation cites per cell line. Of note, while FRP1 expression had no effect on tumor growth induced by parental cells, it caused a striking reduction in the tumor forming ability of β-catenin wild type allele containing cells (FIG. 7F). All of these findings establish that autocrine Wnt signaling can be present in human colon carcinoma cells that harbor downstream lesions within the canonical pathway.

Example 11

Localization of β-Catenin in 293T and H23 Non-Small Cell Lung Carcinoma Tumor Cells Uncomplexed cytoplasmic β-catenin is known to translocate to the nucleus and activate transcription through heterodimerization with a member of the TCF/LEF family of transcription factors. (Giles et al. (2003) *Biochim. Biophys. Acta* 1653:1-24). We have analyzed some autocrine Wnt human tumor cell lines in comparison with 293T cells by immunostaining followed by confocal microscopy. Sub-confluent cultures of 293T (ATCC No. CRL-11268) and H23 (ATCC No. CRL-5800) non-small cell lung carcinoma (NSCLC) tumor cells were fixed with formaldehyde and stained with the anti-β-catenin antibody (Transduction Laboratories) followed by a FITC-labeled secondary antibody (Vector Laboratories, Burlinggame, Calif.).

Figure 8:
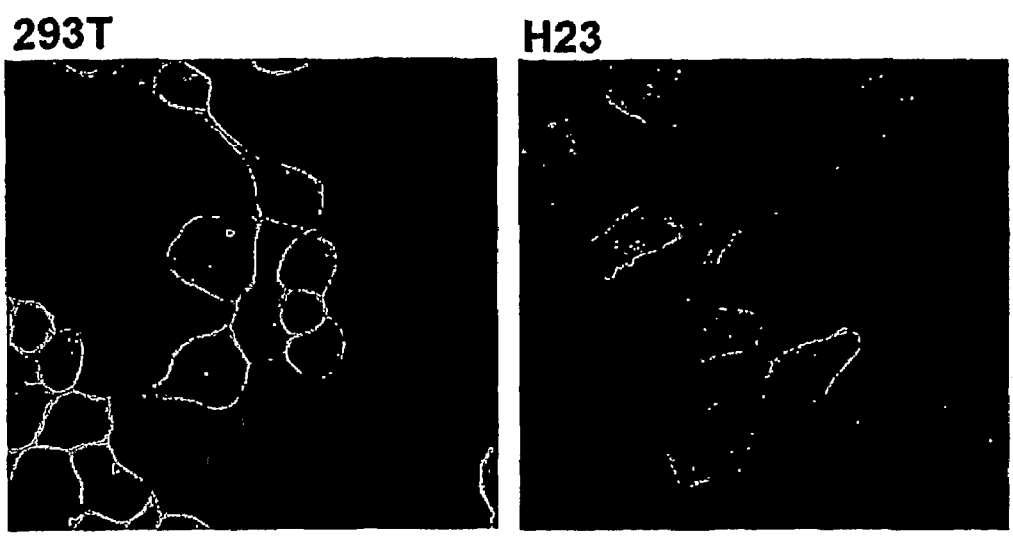
FIG. 8 shows β-catenin staining of 293T and H23 non-small cell lung carcinoma 5 tumor cells. Sub-confluent cultures of 293T and H23NSCLC cell lines were fixed with formaldehyde and stained with anti-β-catenin antibody followed by a FITC-labeled secondary antibody. Nuclei were stained with DAPI.

Nuclei were stained with DAPI (Vector Laboratories). From the results of the β-catenin staining of 293T and H23NSCLC tumor cells, we have further shown that β-catenin can be detected in the cytoplasms and nuclei of H23NSCLC tumor cells (FIG. 8). These findings further establish that β-catenin is present within the sub-cellular location required for it to act as a transcription factor. Finally, we have demonstrated TCF dependent transcriptional reporter activity and the ability of FRP and/or DKK to downregulate this activity in autocrine Wnt lung tumor cells as well as breast/ovarian tumor cells (data not shown). All of these findings broaden the number of tumor types that can exhibit constitutive autocrine Wnt signaling and demonstrate that this mechanism is present in a significant proportion of human breast, lung and ovarian cancers.

Other References of Interest

Alonso and Fuchs (2003) *Genes Dev.* 17:1189-1200; Bafico and Aaronson (2003). Growth factors and signal transduction in cancer. In Cancer Medicine 6, D. W. Kufe, Pollock, R. E., Weichselbaum, R. R., Bast, R. C., Gansler, T. S., Holland J. F, Frei E, ed. (Decker, B C), pp. 53-71; Bafico et al. (1999) *J. Biol. Chem.* 274:16180-16187; Bafico et al. (1998) *Oncogene* 16:2819-2825; Bafico et al. (2001) *Nat. Cell Biol.*

3:683-686; Bejcek et al. (1989) *Science* 245, 1496-1499; Bienz and Clevers (2000), *Cell* 103:311-320; Blasband et al. (1992) *Oncogene* 7:153-161; Blume-Jensen and Hunter (2001) *Nature* 411:355-365; Brown (2001) *Breast Cancer Res.* 3:351-355; Brummelkamp et al. (2002) *Science* 296: 550-553; Bui et al. (1997) *Oncogene* 14, 1249-1253; Cadigan, K. M., and Nusse, R. (1997) *Genes Dev* 11, 3286-3305; Caldwell et al. (2004) *Cancer Res* 64, 883-888; Chan et al. (2002) *Proc Natl Acad Sci USA* 99, 8265-8270; Chen et al. (2001) *J Cell Biol* 152, 87-96; Dale et al. (1996) Cancer Res 56, 4320-4323; Doolittle et al. (1983) Science 221, 275-277; Fedi et al. (1999) *J Biol Chem* 274, 19465-19472; Filali et al. (2002) *J Biol Chem* 277, 33398-33410; Finch et al. (1997) *Proc Natl Acad Sci USA* 94, 6770-6775; Giles et al. (2003) Biochim Biophys Acta 1653, 1-24; Glinka et al. (1998) Nature 391, 357-362; Going (2003) *J. Pathol.* 199:1-3; He et al. (1998) Science 281, 1509-1512; Huang et al. (1984) Cell 39, 79-87; Hudziak et al. (1989) Mol Cell Biol 9, 1165-1172; Huguet et al. (1994) Cancer Res 54, 2615-2621; Hulsken et al. (1994) J Cell Biol 127, 2061-2069; Kawano and Kypta (2003) J Cell Sci 116, 2627-2634; Keating and Williams (1988) Science 239, 914-916; Kuhnert et al. (2004) Proc Natl Acad Sci USA 101, 266-271; Lee and Donoghue (1992) J Cell Biol 118, 1057-1070; Lepourcelet et al. (2004) Cancer Cell 5, 91-102; Leyns et al. (1997) Cell 88, 747-756; Li et al. (2003) Proc Natl Acad Sci USA 100, 15853-15858; Lin et al. (1997) Proc Natl Acad Sci USA 94, 11196-11200; Lin et al. (2000) Proc Natl Acad Sci USA 97, 4262-4266; Liu et al. (2004) Proc Natl Acad Sci USA; Liu et al. (2003) Mol Cell Biol 23, 5825-5835; Longo et al. (2002) J Biol Chem 277, 38239-38244; Macip et al. (2003) Mol Cell Biol 23, 8576-8585; Mao et al. (2002) Nature 417, 664-667; Mao et al. (2001) Nature 411, 321-325; Morin et al. (1997) Science 275, 1787-1790; Myers et al. (1992) J Clin Oncol 10, 881-889; Nusse and Varmus (1992) Cell 69, 1073-1087; Orford et al. (1999) J Cell Biol 146, 855-868; Palacios and Gamallo (1998) Cancer Res 58, 1344-1347; Pierce et al. (1991) Oncogene 6, 1189-1194; Pinson et al. (2000) Nature 407, 535-538; Pinto et al. (2003) Genes Dev 17, 1709-1713; Polakis (2000) Genes Dev 14, 1837-1851; Polesskaya et al. (2003) Cell 113, 841-852; Rattner et al. (1997) Proc Natl Acad Sci USA 94, 2859-2863; Reya et al. (2003) Nature 423, 409-414; Rockman et al. (2001) J Biol Chem 276, 45113-45119; Rowlands et al. (2003) Proc Natl Acad Sci USA 100:11400-11405; Sagae et al. (1999) Jpn J Cancer Res 90, 510-515; Sekine et al. (2002) Oncogene 21, 5906-5911; Semenov et al. (2001) Curr Biol 11, 951-961; Shimizu et al. (1997) Cell Growth Differ 8, 1349-1358; Shtutman et al. (1999) Proc Natl Acad Sci USA 96, 5522-5527; Siu et al. (1999) Cancer Res 59, 63-66; Slamon et al. (2001) N Engl J Med 344, 783-792; Staal et al. (2002) EMBO Rep 3, 63-68; Stampfer and Bartley (1985) Proc Natl Acad Sci USA 82, 2394-2398; Stingl et al. (2001) Breast Cancer Res Treat 67, 93-109; Sugrue et al. (1997) Proc Natl Acad Sci USA 94, 9648-9653; Suzuki et al. (2002) Nat Genet. 31, 141-149; Suzuki et al. (2004) Nat Genet; Tetsu and McCormick (1999) Nature 398, 422-426; van de Wetering et al. (2002a) Cell 109 Suppl, S13-19; van de Wetering et al. (2002b) Cell 111, 241-250; van Noort et al. (2002) J Biol Chem 277, 17901-17905; Wang et al. (1997) Cell 88, 757-766; Waterfield et al. (1983) Nature 304, 35-39; Wehrli et al. (2000) Nature 407, 527-530; Wiley et al. (1998) J Cell Biol 143:1317-1328; Wong et al. (1994) Mol Cell Biol 14, 6278-6286; Wu et al. (2001) Cancer Res 61, 8247-8255; You et al. (2002) J Cell Biol 157, 429-440; and Yu, Q., Geng, Y., and Sicinski, P. (2001) Nature 411, 1017-1021.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It should be further understood that all values are approximate, and are provided for description.

What is claimed is:

1. A method for inhibiting growth of a tumor cell, which tumor cell has active autocrine Wnt signaling and is selected from the group consisting of breast cancer cell, ovarian cancer cell, and Non-Small Cell Lung Carcinoma (NSCLC) cell, comprising contacting said tumor cell with a Wnt receptor antagonist, wherein the Wnt receptor antagonist inhibits said autocrine Wnt signaling.

2. The method of claim 1, wherein the Wnt receptor antagonist is an antisense RNA or an siRNA.

3. The method of claim 1, wherein the Wnt receptor antagonist is Dickkopf-1 (DKKI).

4. The method of claim 2, wherein the Wnt receptor antagonist is an siRNA specific for low density lipoprotein receptor-related protein 5 (LRP5) or lipoprotein receptor-related protein 6 (LRP6).

5. The method according to any one of claim 1, 2, 3, or 4 wherein the Wnt receptor antagonist induces or enhances apoptosis in said tumor cell.

6. The method of claim 1 wherein the tumor cell is an ovarian cancer cell.

7. The method of claim 1, wherein the tumor cell is a breast cancer cell.

8. The method of claim 1, further comprising contacting the tumor cell with a chemotherapeutic agent.

9. The method of claim 1, further comprising contacting the tumor cell with radiation.

10. The method of claim 1 wherein the inhibited Wnt signaling is detected as a reduction in uncomplexed β-catenin levels.

11. A method for sensitizing a tumor cell to a treatment, which tumor cell has active autocrine Wnt signaling and is selected from the group consisting of breast cancer cell, ovarian cancer cell, and Non-Small Cell Lung Carcinoma (NSCLC) cell, comprising contacting said tumor cell with a Wnt receptor antagonist, wherein the Wnt receptor antagonist inhibits said autocrine Wnt signaling.

12. The method of claim 11 wherein the Wnt receptor antagonist is an antisense RNA or an siRNA.

13. The method of claim 11 wherein the Wnt receptor antagonist is Dickkopf-1 (DKKI).

14. The method of claim 12, wherein the Wnt receptor antagonist is an siRNA specific for low density lipoprotein receptor-related protein 5 (LRP5) or lipoprotein receptor-related protein 6 (LRP6).

15. The method according to anyone of claims 11, 12, 13, or 14 wherein the Wnt receptor antagonist induces or enhances apoptosis in said tumor cell.

16. The method of claim 11 wherein the tumor cell is an ovarian cancer cell.

17. The method of claim 11 wherein the tumor cell is a breast cancer cell.

18. The method of claim 11, wherein the treatment is a chemotherapy.

19. The method of claim 11, wherein the treatment is a radiation therapy.

20. The method of claim 11, wherein the inhibited Wnt signaling is detected as a reduction in uncomplexed β-catenin levels.

21. The method of claim 1 or claim 11 wherein the Wnt receptor antagonist is formulated as a pharmaceutical composition, comprising the Wnt receptor antagonist and a pharmaceutically acceptable carrier or excipient.

* * * * *

UNITED STATES PATENT AND TRADEMARK OFFICE
CERTIFICATE OF CORRECTION

PATENT NO. : 8,809,287 B2
APPLICATION NO. : 11/719327
DATED : August 19, 2014
INVENTOR(S) : Anna Bafico et al.

It is certified that error appears in the above-identified patent and that said Letters Patent is hereby corrected as shown below:

In the Specification

Column 1, Line 3

Below the title, insert the heading -- GOVERNMENT SUPPORT -- therefor.

Below the above heading, insert -- This invention was made with government support under Grant No. CA071672 awarded by the National Institutes of Health. The government has certain rights in the invention -- therefor.

Signed and Sealed this
Twenty-fifth Day of November, 2014

Michelle K. Lee
*Deputy Director of the United States Patent and Trademark Office*

SEQUENCE LISTING

```
<160> NUMBER OF SEQ ID NOS: 9

<210> SEQ ID NO 1
<211> LENGTH: 19
<212> TYPE: DNA
<213> ORGANISM: artificial
<220> FEATURE:
<223> OTHER INFORMATION: Synthetic oligonucleotide

<400> SEQUENCE: 1
ccgcatggtg attgatgaa                                                 19

<210> SEQ ID NO 2
<211> LENGTH: 21
<212> TYPE: DNA
<213> ORGANISM: artificial
<220> FEATURE:
<223> OTHER INFORMATION: Synthetic oligonucleotide

<400> SEQUENCE: 2
tggctccctc tgctcttgac c                                              21

<210> SEQ ID NO 3
<211> LENGTH: 21
<212> TYPE: DNA
<213> ORGANISM: artificial
<220> FEATURE:
```

```
<223> OTHER INFORMATION: Synthetic oligonucleotide

<400> SEQUENCE: 3
agtcaatgtt atcactgcag c                                          21

<210> SEQ ID NO 4
<211> LENGTH: 22
<212> TYPE: DNA
<213> ORGANISM: artificial
<220> FEATURE:
<223> OTHER INFORMATION: Synthetic oligonucleotide

<400> SEQUENCE: 4
gaaggctgga agtggggcgg ct                                         22

<210> SEQ ID NO 5
<211> LENGTH: 24
<212> TYPE: DNA
<213> ORGANISM: artificial
<220> FEATURE:
<223> OTHER INFORMATION: Synthetic oligonucleotide

<400> SEQUENCE: 5
gtctccaccc agcctcggga ctca                                       24

<210> SEQ ID NO 6
<211> LENGTH: 23
<212> TYPE: DNA
<213> ORGANISM: artificial
<220> FEATURE:
<223> OTHER INFORMATION: Synthetic oligonucleotide

<400> SEQUENCE: 6
ggatacttct tactcctctg cag                                        23

<210> SEQ ID NO 7
<211> LENGTH: 23
<212> TYPE: DNA
<213> ORGANISM: artificial
<220> FEATURE:
<223> OTHER INFORMATION: Synthetic oligonucleotide

<400> SEQUENCE: 7
aatggcgtgg acaaaggccg act                                        23

<210> SEQ ID NO 8
<211> LENGTH: 19
<212> TYPE: DNA
<213> ORGANISM: artificial
<220> FEATURE:
<223> OTHER INFORMATION: Synthetic oligonucleotide

<400> SEQUENCE: 8
ccgcatggtg attgatgaa                                             19

<210> SEQ ID NO 9
<211> LENGTH: 19
<212> TYPE: DNA
<213> ORGANISM: artificial
<220> FEATURE:
<223> OTHER INFORMATION: Synthetic oligonucleotide

<400> SEQUENCE: 9
catgatcgag tcgtccaac                                             19
```